(12) United States Patent
Collier et al.

(10) Patent No.: US 9,399,090 B2
(45) Date of Patent: Jul. 26, 2016

(54) POTASSIUM LOADED ION-EXCHANGE MATERIAL FOR USE IN A DIALYSATE REGENERATION SYSTEM

(71) Applicants: Kenneth J. Collier, Dellwood, MN (US); Martin T. Gerber, Maple Grove, MN (US); David B. Lura, Maple Grove, MN (US); Thomas E. Meyer, Stillwater, MN (US); Bryant J. Pudil, Plymouth, MN (US)

(72) Inventors: Kenneth J. Collier, Dellwood, MN (US); Martin T. Gerber, Maple Grove, MN (US); David B. Lura, Maple Grove, MN (US); Thomas E. Meyer, Stillwater, MN (US); Bryant J. Pudil, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 154 days.

(21) Appl. No.: 13/757,796

(22) Filed: Feb. 2, 2013

(65) Prior Publication Data
US 2014/0158538 A1    Jun. 12, 2014

Related U.S. Application Data

(60) Provisional application No. 61/735,359, filed on Dec. 10, 2012.

(51) Int. Cl.
| A61M 1/16 | (2006.01) |
| B01D 61/24 | (2006.01) |
| B01D 61/26 | (2006.01) |
| B01D 61/42 | (2006.01) |
| B01D 61/32 | (2006.01) |
| B01D 61/54 | (2006.01) |
| A61M 1/28 | (2006.01) |

(52) U.S. Cl.
CPC .......... *A61M 1/1656* (2013.01); *A61M 1/1654* (2013.01); *A61M 1/1696* (2013.01); *A61M 1/287* (2013.01); *A61M 2205/3317* (2013.01)

(58) Field of Classification Search
None
See application file for complete search history.

(56) References Cited

U.S. PATENT DOCUMENTS

| 3,669,880 | A | | 6/1972 | Marantz |
| 3,850,835 | A | | 11/1974 | Marantz |
| 3,989,622 | A | | 11/1976 | Marantz |
| 4,269,708 | A | | 5/1981 | Bonomini |
| 4,460,555 | A | | 7/1984 | Thompson |
| 4,581,141 | A | | 4/1986 | Ash |
| 4,650,587 | A | | 3/1987 | Polak |
| 5,954,937 | A | * | 9/1999 | Farmer .......................... 205/687 |
| 6,627,164 | B1 | | 9/2003 | Wong |
| 6,818,196 | B2 | | 11/2004 | Wong |
| 7,566,432 | B2 | | 7/2009 | Wong |
| 2004/0079704 | A1 | * | 4/2004 | Garde et al. ................... 210/649 |
| 2007/0179431 | A1 | * | 8/2007 | Roberts et al. ................... 604/29 |

(Continued)

FOREIGN PATENT DOCUMENTS

WO    2009157877    12/2009

OTHER PUBLICATIONS

EP13182115.9-1651 European Search Report, Feb. 3, 2014.

*Primary Examiner* — Krishnan S Menon
*Assistant Examiner* — Bradley R Spies
(74) *Attorney, Agent, or Firm* — Hahn & Associates PLLC; Roger C. Hahn

(57) ABSTRACT

Systems and methods for managing the potassium concentration of a dialysate fluid during hemodialysis therapy using cation exchange materials that do not release sodium ions.

37 Claims, 11 Drawing Sheets

(56) References Cited

U.S. PATENT DOCUMENTS

| | | |
|---|---|---|
| 2010/0007838 A1 | 1/2010 | Fujimoto |
| 2010/0010429 A1 | 1/2010 | Childers |
| 2010/0078381 A1 | 4/2010 | Merchant |
| 2010/0084330 A1 | 4/2010 | Wong |
| 2011/0030967 A1* | 2/2011 | McGuire .............. B01J 49/0069 166/369 |
| 2011/0048949 A1 | 3/2011 | Ding et al. |
| 2011/0123604 A1* | 5/2011 | Strickland et al. ............ 424/451 |
| 2012/0273354 A1* | 11/2012 | Orhan et al. .................. 204/519 |
| 2013/0199998 A1 | 8/2013 | Kelly |

* cited by examiner

POTASSIUM LOADED ION-EXCHANGE MATERIAL FOR USE IN A DIALYSATE REGENERATION SYSTEM

FIELD OF THE INVENTION

The invention relates to systems for managing the potassium concentration of a dialysate fluid during hemodialysis therapy using cation exchange materials that do not release sodium ions.

BACKGROUND

During hemodialysis, the dialysate sodium concentration plays a role in patient outcomes. Performing hemodialysis on a patient with specific dialysate sodium ion concentrations can influence the occurrence of hypotensive episodes, the prevention of disequilibrium syndrome, and the minimization of interdialytic weight gain, among other things. Methods and systems to manage sodium dialysate concentration are important with systems that contain a component that may change the sodium ion level to unknown values. For example, regenerative hemodialysis systems, such as the Recirculating Dialysate System ("REDY" System), contain sorbent materials that release and/or remove sodium from the dialysate fluid. The removal and/or addition of sodium to the dialysate fluid depend on several factors including: patient blood urea level, patient weight, dialysate composition, sorbent properties, etc. Because of this, it becomes difficult to predict the changes in dialysate sodium concentration that will occur during a hemodialysis session.

Expensive sorbent materials can be depleted, and also necessitate complicated management systems to monitor sodium concentration of the dialysate fluid exiting the sorbent system. For example, the "REDY" system requires 6 to 8 liters of water for operation and in some cases the patient is required to remove 1 to 2 liters of dialysate during operation and replace with 1 to 2 liters of fresh water in order to reduce the sodium levels in the dialysate. Increases in sodium ion concentration of a working dialysate become difficult to predict during hemodialysis treatment. As such, there is a need for eliminating system components that contribute to increases in sodium ion concentrations. There is also a need for a system having reduced sodium levels in the dialysate fluid prior to entering a regenerative dialysate system such that the amount of sodium released by a sorbent system is low. There is a related need for systems and methods that do not require sodium control or only require simplified or minimal management. Further, there is a need for systems and methods that can control the sodium concentration of the dialysate by removing or adding sodium ions from a working dialysate. There is also a need for methods for managing sodium that minimize system size and weight and do not require large amounts of water.

In addition to being in danger of exposure to the complications of unknown sodium levels during dialysis sessions, some kidney patients can experience an extreme variation of potassium levels during their dialysis sessions that increases their health risk. During hemodialysis, there is a net addition of base in the form of bicarbonate, which increases the cellular uptake of potassium and attenuates the overall removal of potassium from the cells. Hence, patients may initially experience an increase in their intracellular potassium levels followed by a reduction in levels resulting in hypokalemia. This condition is of particular concern to patients with underlying cardiac conditions. As such, there is an unmet need to guard against risk to patients during dialysis sessions by monitoring potassium and more tightly controlling potassium levels, as well as to more efficiently manage sodium levels. There is also a need for methods and systems to determine the potassium dialysate concentration, particularly where the dialysis system itself contains a component that affects the potassium concentration in the dialysate fluid.

SUMMARY OF THE INVENTION

The present invention describes a system for kidney replacement therapy that can have a dialysate flow loop for circulating a dialysate through a dialyzer where at least one waste species can enter the dialysate and has a dialysate regeneration unit for decreasing the concentration or conductivity of the at least one waste species and releasing at least one conductive species to the dialysate or absorbing at least one conductive species from the dialysate. An optional potassium ion or conductivity detector can measure the conductivity or potassium ion concentration of the dialysate, and a potassium management system can modify a potassium ion concentration of the dialysate in the dialysate flow loop where the potassium-modified fluid can have a potassium ion concentration or conductivity that is higher or lower than the fluid in the dialysate flow loop.

In any embodiment, an optional potassium ion or conductivity detector can measure the conductivity or potassium ion concentration of the dialysate. In other embodiments, a potassium ion sensor is not required because sorbent removes substantially all of the potassium in the dialysate.

In any embodiment, the system for kidney replacement therapy can be controlled compliant. In any embodiment, the system for kidney replacement therapy can selectively meter fluid into and out of the dialysate flow loop. In any embodiment, the system for kidney replacement therapy can selectively meter fluid into and out of the dialysate flow loop using any one of a control pump, a water pump, a salination pump, an acid concentrate pump, a replacement fluid pump, and combinations thereof. In any embodiment, the system for kidney replacement therapy can for bi-directional flow.

A method for modifying the potassium concentration of a dialysate is also described. The method can circulate a dialysate in a dialysate flow loop wherein the dialysate contacts a dialyzer and a dialysate regeneration unit, where a waste species enters the dialysate at the dialyzer and is at least partially removed by the dialysate regeneration unit, modifying the potassium concentration of a provided input fluid using a potassium management system; and adding the potassium-modified fluid to the dialysate flow loop to modify the potassium concentration of the dialysate within the dialysate flow loop.

In any embodiment, the method for regenerating a dialysate can be controlled compliant. In any embodiment, the method for regenerating a dialysate can be provided such that fluid is selectively metered into and out of the dialysate flow loop. In any embodiment, the method for regenerating a dialysate can be provided such that the fluid is selectively metered into and out of the dialysate flow loop using any one of a control pump, a water pump, a salination pump, an acid concentrate pump, a replacement fluid pump, and combinations thereof. In any embodiment, the method for regenerating a dialysate can be provided such that bi-directional flow is provided with the dialysate flow loop.

Systems and methods are described for modifying the sodium concentration of a dialysate wherein certain embodiments of the systems and methods comprise a deionization resin to lower the sodium concentration of a dialysate entering a potassium management system.

In certain embodiments, the potassium concentration of an input fluid provided to the dialysate regeneration unit can be modified by application of an electrical field to generate a potassium-modified fluid. The potassium-modified fluid can be added to the dialysate flow loop to increase or decrease the potassium ion concentration. Alternatively, the potassium-modified fluid can be generated using a potassium management system that modifies the potassium ion concentration of a fluid entering the potassium management system through application of an electrical field. In still other embodiments, the potassium-modified fluid can be generated from solid potassium. The potassium management system can further contain or interoperate with a deionization resin to lower the potassium ion concentration of the dialysate.

In any embodiment, a method or system to control the potassium concentration of a dialysate can use electrodialysis.

In any embodiment, a method or system to control the potassium ion concentration of a dialysate can use capacitive deionization.

In any embodiment, a method or system to control the potassium ion concentration of a dialysate can use capacitive deionization or electrodialysis.

In any embodiment, a method or system contains a sorbent material for removing remaining potassium in the dialysate that avoids the need for monitoring or managing sodium in the dialysate. The method or system can also avoid the need for potassium monitoring or control.

In any embodiment, a method or system to control the potassium ion concentration of a dialysate can modify the potassium ion concentration from a stream coming from a dialysate or with electrodialysis and can use the resulting fluid for potassium ion adjustment.

In any embodiment, a method or system to control the potassium ion concentration of a dialysate modifies the potassium concentration from a stream coming from a dialysate or with capacitive deionization and can use the resulting fluid for potassium ion adjustment.

In any embodiment, the methods or systems described herein for potassium ion concentration modification can provide for the addition of a potassium-modified fluid upstream or downstream from a dialysate regeneration unit.

BRIEF DESCRIPTION OF THE DRAWINGS

Throughout the figures and the specification, components with the same numbers in the FIG.'s refer to the same components.

DETAILED DESCRIPTION

Definitions

Figure 1:
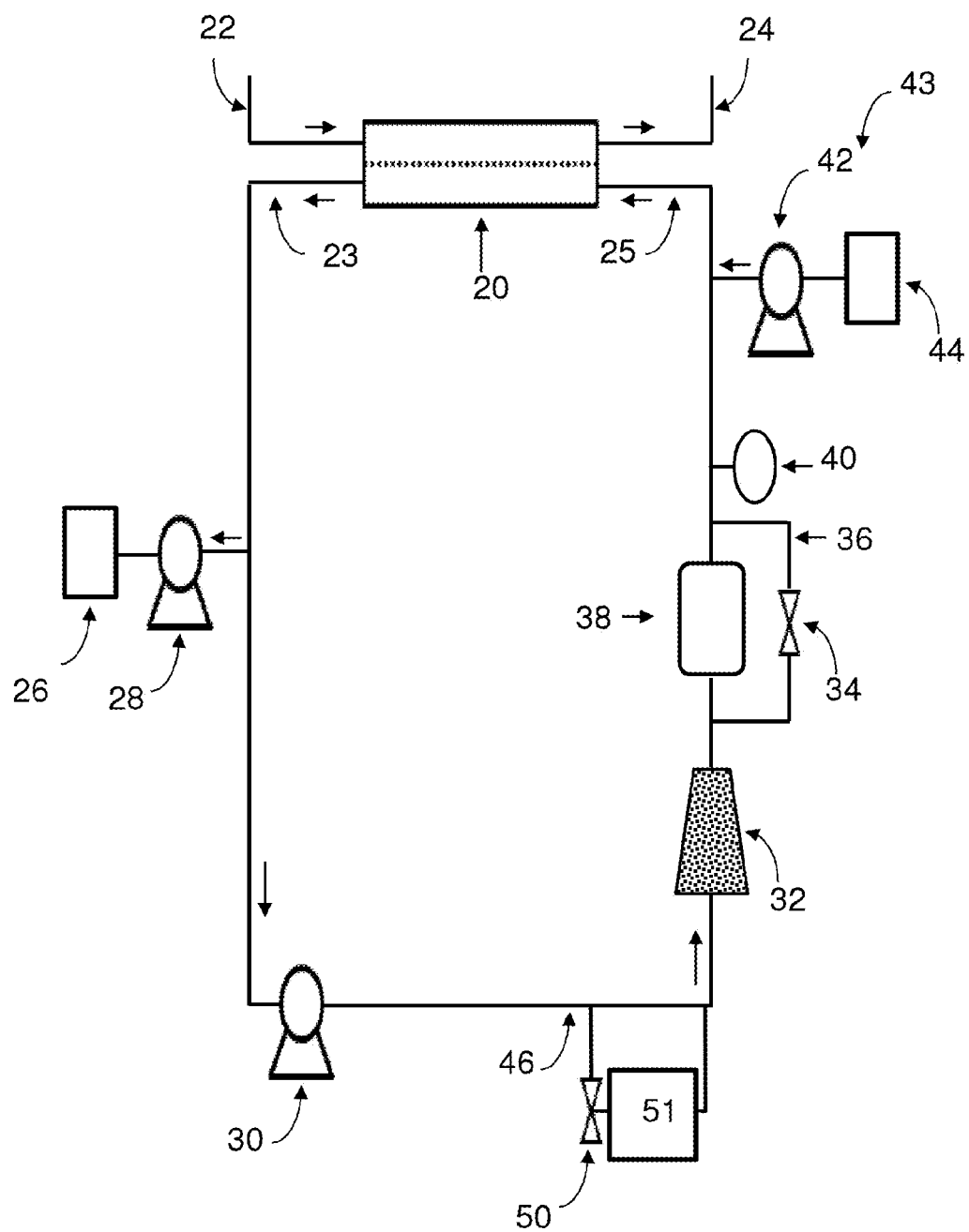
FIG. 1 is a flow diagram of a dialysate regeneration system with a controlled compliant dialysate circuit and a potassium management system.

Unless defined otherwise, all technical and scientific terms used herein generally have the same meaning as commonly understood by one of ordinary skill in the relevant art. The definitions provided herein should not be rigidly construed without taking into account the context and other ascribed meanings provided, or by their use, in other parts of the specification, claims, and drawings.

The articles "a" and "an" are used herein to refer to one or to more than one (i.e., to at least one) of the grammatical object of the article. By way of example, "an element" means one element or more than one element.

The term "acid or base equivalents" refers to an equivalent acid or base donating or accepting an equal number of moles of hydrogen or hydronium ions per mole of the acid to which the equivalent acid is being equated, or mole of hydroxide ions to which the equivalent base is being equated.

The term "cation infusate pump" historically known as an "acid concentrate pump" in dialysis systems refers to a pump that serves the function to move or control the flow of a fluid to and/or from a reservoir having a substance that contains at least one cation species, such as calcium, magnesium and potassium ions. In the present invention, the historically used term of "acid concentrate pump" is used.

The term "acid feed" refers a state of fluid communication that enables an acid solution to be obtained from an acid source and connected or feed into a receiving source or flow path.

An "acid" can be either an Arrhenius acid, a Brønsted-Lowry acid, or a Lewis acid. The Arrhenius acids are substances or fluids which increase the concentration of hydronium ions ($H3O+$) in solution. The Brønsted-Lowry acid is a substance which can act as a proton donor. Lewis acids are electron-pair acceptors.

The term "activated carbon" may refer to a porous carbon material having a surface area greater than 500 $m^2$ per gram. Activated carbon can be capable of absorbing several species including heavy metals such as lead, mercury, arsenic, cadmium, chromium and thallium among others, oxidants such as chlorine and chloramines, fluoride ions, and waste species such as phosphate and certain nitrogen-containing waste species such as creatinine and uric acid.

The terms "administering," "administer," "delivering," "deliver," "introducing," and "introduce" can be used, in context, interchangeably to indicate the introduction of water or a dialysate having an altered concentration of at least one component, including electrolytes and alkali and/or alkali earth ions, to a patient in need thereof, and can further mean the introduction of water, any agent or alkali and/or alkali earth ions to a dialysate or dialysis circuit where such water, agent or alkali and/or alkali earth ion will enter the blood of the patient by diffusion, transversal of a diffusion membrane or other means.

The term "air trap" refers to a structure for separating a gas from a mixture of a gas and a liquid or any other separation means known in the art. An air trap can include a hydrophobic membrane for allowing gases to pass and for preventing the passage of water.

The term "albumin sieving coefficient" can be used to describe the amount of albumin that will cross a membrane.

The terms "ammonia sensing module" and "ammonia detector" refer to a unit that performs all or part of the function to detect a predetermined level of, or measure a concentration of, ammonia and/or ammonium ions in a fluid.

The term "anion exchange membrane" refers to a positively charged membrane, which allows negatively charged ions (anions) to pass through.

The term "anticoagulant" is a substance that prevents or delays the clotting of blood, such as heparin, Fragmin®, and sodium citrate.

The term "atmospheric pressure" refers to the local pressure of air in the environment in proximity to the system at the time that the system is operating.

The term "base concentrate pump" refers to a device that performs work on a fluid solution to cause fluid flow to control the volume transfer of a basic or alkaline solution into a circuit.

The term "base concentrate reservoir" refers to a vessel or container, optionally accessible by a pump that contains a variable amount of a basic or alkaline fluid solution.

The term "base module" refers to a basic unit of an apparatus for hemodialysis, hemodiafiltration, or hemofiltration that incorporates one or more fluid pathways. Exemplary, non-limiting components that can be included in the base module include conduits, valves, pumps, fluid connection ports, sensing devices, a controller and a user interface. The base module can be configured to interface with reusable or disposable modules of the apparatus for hemodialysis, hemodiafiltration, or hemofiltration to form at least one complete fluid circuit, such as a dialysis, cleaning, disinfection, priming or blood rinse back circuit.

A "base" can be either a substance that can accept hydrogen cations (protons) or more generally, donate a pair of valence electrons. A soluble base is referred to as an alkali if it contains and releases hydroxide ions (OH—) quantitatively. The Brønsted-Lowry theory defines bases as proton (hydrogen ion) acceptors, while the more general Lewis theory defines bases as electron pair donors, allowing other Lewis acids than protons to be included.[1] The Arrhenius bases act as hydroxide anions, which is strictly applicable only to alkali.

The term "base feed" refers a state of fluid communication that enables a base solution to be obtained from a base source and connected or feed into a receiving source or flow path.

The term "bicarbonate buffer component" refers to any composition contain bicarbonate (HCO3−) ion or a conjugate acid of bicarbonate ion in any amount, proportion or pH of the composition. The bicarbonate buffering system is an important buffer system in the acidbase homeostasis of living things, including humans. As a buffer, it tends to maintain a relatively constant plasma pH and counteract any force that would alter it. In this system, carbon dioxide (CO2) combines with water to form carbonic acid (H2CO3), which in turn rapidly dissociates to form hydrogen ions and bicarbonate (HCO3−) as shown in the reactions below. The carbon dioxide -carbonic acid equilibrium is catalyzed by the enzyme carbonic anhydrase; the carbonic acid -bicarbonate equilibrium is simple proton dissociation/association and needs no catalyst.)

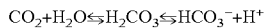

$$CO_2 + H_2O \leftrightarrows H_2CO_3 \leftrightarrows HCO_3^- + H^+$$

Any disturbance of the system will be compensated by a shift in the chemical equilibrium according to Le Chatelier's principle. For example, if one attempted to acidify the blood by dumping in an excess of hydrogen ions (acidemia), some of those hydrogen ions will associate with bicarbonate, forming carbonic acid, resulting in a smaller net increase of acidity than otherwise.

The term "bicarbonate buffer concentrate" refers to a bicarbonate ($HCO_3^-$) buffer component composition at a higher concentration than found at normal physiological levels that can be used to for instants to readjusted the pH of the dialysate (see also definition of bicarbonate buffer component relating to its use).

The term "bicarbonate cartridge" refers to a container that can be a stand-alone container or alternatively can be integrally formed with an apparatus for hemodialysis, hemodiafiltration, or hemofiltration. The bicarbonate cartridge can store a source of buffering material, such as sodium bicarbonate, and can be configured to interface with at least one other functional module found in systems for hemodialysis, hemodiafiltration, or hemofiltration. For example, the bicarbonate cartridge can contain at least one fluid pathway and include components such as conduits, valves, filters or fluid connection ports. The bicarbonate cartridge can be disposable or be consumable wherein the cartridge is recharged upon depletion. Specifically, the term "bicarbonate consumables container" refers to an object or apparatus having or holding a material in solid and/or solution form that is a source of bicarbonate, such as sodium bicarbonate, that is depleted during operation of the system. The object or apparatus may be single use, or may be replenished and used multiple times, for example, by refilling the object to replace the consumed material.

The term "bicarbonate feed" refers to fluid solution introduced into part of the dialysis or ultrafiltrate system. For example a "bicarbonate feed" is a conduit that contains a bicarbonate buffer concentrate that is used to readjust the pH of the dialysate.

The term "bidirectional pump" refers to a device configured to perform work on a fluid to cause the fluid to flow alternatively in either of two opposing directions.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The term "bipolar electrodialysis system" refers to an electrochemical separation process in which ions are selectively transferred through a bipolar membrane.

The term "bipolar membrane" refers to a membrane formed by bonding an anion exchange and a cation exchange membrane together wherein the membranes result in the dissociation of water into hydrogen ions. The anion- and cation-exchange membranes can either be bound together physically or chemically such that the bipolar membrane has a thin interface where water diffuses into the membrane from outside aqueous salt solutions.

The term "blood access connection" refers to a junction or aperture through which the blood of a subject is conveyed to or from an extracorporeal circuit. Commonly, the blood access connection is made between a terminal end of a conduit of an extracorporeal circuit and the terminal end of a catheter or fistula needle that is distal to the subject receiving therapy. A subject may have more than one blood access connection when receiving therapy. In the case of two blood access connections they can be referred to as an arterial blood access connection and a venous blood access connection.

The term "blood solute" refers to a substance dissolved, suspended, or present in blood or dialysate.

The term "bolus" refers to an increase (or at times a decrease) of limited duration in an amount or concentration of one or more solutes, for example sodium, glucose and potassium, or a solvent, for example water, such that the concentration of a solution is changed. The term "bolus" includes delivery of solute and/or solvent to the dialysate fluid path such that it is delivered to the blood of a subject via diffusion and/or convection across a dialysis membrane such that the amount or concentration in the subject is increased or decreased. A "bolus" may also be delivered directly to the extracorporeal flow path or the blood of a subject without first passing through the dialysis membrane.

The term "bottled water" refers to water that may be filtered or purified and has been packaged in a container. Bottled water can include water that has been packaged and provided to a consumer as drinking water.

The term "breakthrough capacity" refers to the amount of solute a sorbent material can remove until breakthrough occurs. Breakthrough occurs when the concentration of a certain solute exiting a regeneration module becomes non-zero.

The terms "bubble detector," "bubble sensor," "gas detector" and "air detector" refer to a device that can detect the presence of a void, void space, or gas bubble in a liquid.

The term "buffer conduit flow path" refers to a fluid flow path in fluid communication with a stored source of a buffering material, such as bicarbonate.

The term "buffer source" refers to a stored material, such as bicarbonate, acetate or lactate that provides buffering.

The terms "buffer source container" and "buffer source cartridge" refer to objects that have or hold one or more materials, in solid and/or solution form, that are a source of buffering, for example a bicarbonate, a lactate, or acetate; and the object further having at least one port or opening to allow at least a portion of the buffering material to be released from the object during operation of the system.

The term "blood based solute monitoring system" refers to a system for monitoring a substance dissolved or suspended or present in blood or dialysate.

The term "blood rinse back" refers to returning the blood from a dialyzer and/or extracorporeal circuit to a subject, normally at conclusion of a therapy session and prior to disconnecting or removing the subject's blood access connection or connections. The procedure can include conveying a physiologically compatible solution through the extracorporeal circuit to push or flush the blood from the extracorporeal circuit to the subject via the subject's blood access connection or connections.

The terms "bypass circuit" "bypass conduit," "bypass flow path," "bypass conduit flow path" and "bypass" refer to a component or collection of components configured or operable to create an alternate fluid pathway to convey a fluid around one or more other components of a fluid circuit such that at least a portion of the fluid does not contact or pass through the one or more other components. At times the term "shunt" may be used interchangeable with the term "bypass." When any of the above "bypass" terms listed in this paragraph are used in context as being part of a controlled compliant system, then the relevant referenced "bypass" has the proper characteristics as to operate within a controlled compliant system as defined herein.

The term "bypass regulator" refers to a component such as valve that can determine the amount of fluid that can pass through a by-pass portion of a fluid circuit.

The term "capacitive deionization" refers to a process for directly removing salts from solution by applying an electric field between two electrodes.

The term "cartridge" refers to a compartment or collection of compartments that contains at least one material used for operation of the system of the present invention.

The term "cassette" refers to a grouping of components that are arranged together for attachment to, or use with the device, apparatus, or system. One or more components in a cassette can be any combination of single use, disposable, consumable, replaceable, or durable items or materials.

The term "cation exchange membrane" refers to a negatively charged membrane, which allows positively charged ions (cations) to pass. By convention, electrical current flows from the anode to the cathode when a potential is applied to an electrodialysis cell. Negatively charged anions such as chloride ions are drawn towards the anode, and positively charged cations such as sodium ions are drawn towards the cathode.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid, non-limiting examples can be glucose, dextrose, acetic acid and citric acid.

The term "cation concentrate reservoir" refers to an object having or holding a substance that is comprised of at least one cation, for example calcium, magnesium, or potassium ions.

The terms "communicate" and "communication" include, but are not limited to, the connection of system electrical elements, either directly or remotely, for data transmission among and between said elements. The terms also include, but are not limited to, the connection of system fluid elements enabling fluid interface among and between said elements.

The terms "conduit," "conduit" or "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "counter-current sorbent cartridge" refers to a sorbent cartridge as defined above that includes two inlet and two outlet flow paths. The first inlet and second inlet flow paths are on opposite ends of the sorbent cartridge along the direction of flow through the sorbent cartridge. Likewise, the first outlet and second outlet flow paths are on opposite ends of the sorbent cartridge along the direction of flow through the sorbent cartridge. The first inlet and second outlet are on the same end of the sorbent cartridge. Also, the first outlet and second inlet are on the same end of the sorbent cartridge.

The term "central axis" refers to (a) a straight line about which a body or a geometric figure rotates or may be supposed to rotate; (b) a straight line with respect to which a body or figure is symmetrical—called also axis of symmetry; (c) a straight line that bisects at right angles a system of parallel chords of a curve and divides the curve into two symmetrical parts; or (d): one of the reference lines of a coordinate system.

The term "chelating resins" refers to a class of resins that interacts and selectively binds with selected ions and ligands (the process is referred to as chelation). According to IUPAC, the formation or presence of two or more separate coordinate bonds.

The term "chronic kidney disease" (CKD) refers to a condition characterized by the slow loss of kidney function over time. The most common causes of CKD are high blood pressure, diabetes, heart disease, and diseases that cause inflammation in the kidneys. CKD can also be caused by infections or urinary blockages. If CKD progresses, it can lead to end-stage renal disease (ESRD), where the kidneys fail to function at a sufficient level.

The term "citric acid" refers to an organic acid having the chemical formula $C_6H_8O_7$, and may include anhydrous and hydrous forms of the molecule, and aqueous solutions containing the molecule.

The term "cleaning and/or disinfection concentrate" refers to a dry substance, or concentrated solutions containing at least one material for use in cleaning and/or disinfection of an apparatus.

The term "cleaning and/or disinfection solution" refers to a fluid that is used for the purpose of removing, destroying or impairing at least a portion of at least one contaminant. The contaminant may be organic, inorganic or an organism. The fluid may accomplish the purpose by transmission of thermal energy, by chemical means, flow friction or any combination thereof.

The terms "cleaning manifold" and "cleaning and disinfection manifold" refer to an apparatus that has fluid connection ports and one or more fluid pathways, or fluid port jumpers, that, when connected to jumpered ports of a base module, create one or more pathways for fluid to be conveyed between the jumpered ports of the base module. A cleaning manifold may be further comprised of additional elements, for example valves and reservoirs.

The term "container" as used herein is a receptacle that may be flexible or inflexible for holding fluid or solid, such as for example a spent dialysate fluid, or a sodium chloride or sodium bicarbonate solution or solid.

The terms "common container," "common cartridge," or "common reservoir," and the like refer to an object or apparatus that can hold more than one material; however, the time of holding more than one material may or may not necessarily be at the same time. The material(s) may be in solid and/or solution forms and may be held in separate compartments within the object or apparatus.

The term "common fluid inlet port" refers to an opening or aperture through which all fluid first passes to enter an object, apparatus or assembly.

The term "common fluid outlet port" refers to an opening or aperture through which all fluid passes to exit an object, apparatus or assembly.

The terms "communicate" and "communication" include, but are not limited to, the connection of system electrical elements, either directly or remotely, for data transmission among and between said elements. The terms also include, but are not limited to, the connection of system fluid elements enabling fluid interface among and between said elements.

The terms "component" and "components" refer to a part or element of a larger set or system. As used herein, a component may be an individual element, or it may itself be a grouping of components that are configured as a set, for example, as a cassette or a cleaning and/or disinfection manifold.

The term "comprising" includes, but is not limited to, whatever follows the word "comprising." Thus, use of the term indicates that the listed elements are required or mandatory but that other elements are optional and may or may not be present.

The term "concentrate pump" refers to a device that can perform work on a fluid solution to cause the fluid flow and can actively control the transfer of fluid volume such as an infusate or an acid concentrate, base concentrate, or buffer concentrate into a circuit.

The terms "concentrate flow channel," "concentrate flow loop," "concentrate stream," refer to a fluid line in which ion concentration is increased during electrodialysis.

The terms "conditioning conduit flow path" and "conditioning flow path" refer to a fluid pathway, circuit or flow loop that incorporates a source of a conditioning material, for example a sodium salt or bicarbonate.

The term "conditioning flow path inlet" refers to a location on a conditioning flow path where fluid enters the conditioning flow path The term "conditioning flow path outlet" refers to a location on a conditioning flow path where fluid exits the conditioning flow path.

The terms "conductivity meter," "conductivity sensor," "conductivity detector," conductivity electrode or the like, refer, in context, to a device for measuring the electrical conductance of a solution and/or the ion, such as a sodium ion, concentration of a solution. In specific examples, the conductivity sensor, meter, or conductor can be directed to a specific ion such as sodium and be referred to as a "sodium electrode," "sodium sensor," "sodium detector," or "sodium meter."

The term "conductive species" refers to a material's ability to conduct an electric current. Electrolytes are an example of a conductive species in dialysate fluids, such as, but not limited to the presence sodium, potassium, magnesium, phosphate, and chloride ions. A fluid's ability to conduct an electrical current is due in large part to the ions present in the solution. A fluid's ability to conduct an electrical current is due in large part to the ions present in the solution.

The terms "conduit," "circuit," and "flow path" refer to a vessel or passageway having a void volume through which a fluid can travel or move. A conduit can have a dimension parallel to the direction of travel of the fluid that is significantly longer than a dimension orthogonal to the direction of travel of the fluid.

The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

The term "consisting of" includes and is limited to whatever follows the phrase "consisting of:" Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "consumables" refers to components that are dissipated, wasted, spent or used up during the performance of any function in the present invention. Examples include a quantity of sodium, bicarbonate, electrolytes, infusates, sorbents, cleaning and disinfecting ingredients, anticoagulants, and components for one or more concentrate solutions.

The terms "consumables cartridge" and "consumables container" refer to an object or apparatus having or holding one or more materials that are depleted during operation of the system. The one or more materials may be in solid and/or solution form and can be in separate compartments of the object or apparatus. The object or apparatus may be single use, or may be replenished and used multiple times, for example, by refilling the object to replace the consumed material.

The terms "contact," "contacted," and "contacting" refers, in context, to (1) a coming together or touching of objects, fluids, or surfaces; (2) the state or condition of touching or of immediate proximity; (3) connection or interaction. For example, in reference to a "dialysate contacting a sorbent material" refers to dialysate that has come together, has touched, or is in immediate proximity to connect or interact with any material or material layer of a sorbent container, system or cartridge.

The term "container" as used herein is a receptacle that may be flexible or inflexible for holding fluid or solid, such as for example a spent dialysate fluid, or a sodium chloride or sodium bicarbonate solution or solid, or the like.

The term "contaminant" refers to an undesirable or unwanted substance or organism that may cause impairment of the health of a subject receiving a treatment or of the operation of the system.

The term "control pump," such as for example an "ultrafiltrate pump," refers to a pump that is operable to pump fluid bi-directionally to actively control the transfer of fluid volume into or out of a compartment or circuit.

The terms "control reservoir," "ultrafiltrate reservoir," "solution reservoir," "therapy solution reservoir," and "waste reservoir," as the case may be, refers, in context, to a vessel or container, optionally accessible by a control pump that contains a variable amount of fluid, including fluid that can be referred to as an ultrafiltrate. These reservoirs can function as a common reservoir to store fluid volume from multiple sources in a system. Other fluids that can be contained by these reservoirs include, for example, water, priming fluids, waste fluids, dialysate, including spent dialysate, and mixtures thereof. In certain embodiments, the reservoirs can be substantially inflexible, or non-flexible. In other embodiments, the reservoirs can be flexible containers such as a polymer bag.

The term "control signals" refers to energy that is provided from one element of a system to another element of a system to convey information from one element to another or to cause an action. For example, a control signal can energize a valve actuator to cause a valve to open or close. In another example a switch on a valve can convey the open or close state of a valve to a controller.

A "control system" consists of combinations of components that act together to maintain a system to a desired set of performance specifications. The control system can use processors, memory and computer components configured to interoperate to maintain the desired performance specifications. It can also include fluid control components, and solute control components as known within the art to maintain the performance specifications.

The terms "control valve" and "valve" refer to a device that can be operated to regulate the flow of fluid through a conduit or flow path by selectively permitting fluid flow, preventing fluid flow, modifying the rate of fluid flow, or selectively guiding a fluid flow to pass from one conduit or flow path to one or more other conduits or flow paths.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

A "controller," "control unit," "processor," or "microprocessor" is a device which monitors and affects the operational conditions of a given system. The operational conditions are typically referred to as output variables of the system wherein the output variables can be affected by adjusting certain input variables.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if the patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, and as discussed herein and shown in the drawings is that the controlled compliant system can move fluids bi-directionally. In certain cases, the bi-directional fluid movement is across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

The term "convective clearance" refers to the movement of solute molecules or ions across a semi-permeable barrier due to force created by solvent molecules moving across the semi-permeable barrier.

The terms "controller," "control unit," "processor," and "microprocessor" refers, in context, to a device which monitors and affects the operational conditions of a given system. The operational conditions are typically referred to as output variables of the system wherein the output variables can be affected by adjusting certain input variables.

The terms "coordinately operates" and "coordinately operating" refer to controlling the function of two or more elements or devices so that the combined functioning of the two or more elements or devices accomplishes a desired result.

The term does not exclusively imply that all such elements or devices are simultaneously energized.

The term "deaeration" refers to removing some or all of the air contained in a liquid including both dissolved and non-dissolved air contained in the liquid.

The terms "de-aeration flow path" and "de-aeration flow path" refer to a set of elements that are configured in fluid communication along a fluid flow pathway such that a liquid can be passed through the fluid flow pathway to accomplish removal of some or all of the air or gas contained in the liquid, including removal of air or gas that is dissolved in the liquid.

The terms "degas module" and "degassing module" refer to a component that separates and removes any portion of one or more dissolved or undissolved gas from a liquid. A degas module can include a hydrophobic membrane for allowing ingress or egress of gases through a surface of the module while preventing the passage of liquid through that surface of the module.

The term "deionization resin" refers to any type of resin or material that can exchange one type of ion for another. In one specific case, the term can refer to the removal of ions such as potassium, magnesium, sodium and calcium in exchange for hydrogen and/or hydroxide ions.

The term "detachable" refers to a characteristic of an object or apparatus that permits it to be removed and/or disconnected from another object or apparatus.

The term "dialysate" describes a fluid into or out of which solutes from a fluid to be dialyzed diffuse through a membrane. A dialysate typically contains electrolytes that are close in concentration to the physiological concentration of electrolytes found in blood. A common sodium level for dialysate is ~140 mEq/L. Normal blood sodium levels range from approximately 135 mEq/L to 145 mEq/L. The REDY system typically uses dialysate ranging from 120 mEq/L to 160 mEq/L. In certain embodiment, a "predetermined limit" or "predetermined concentration" of sodium values can be based off the common sodium levels for dialysate and normal blood sodium levels. "Normal" saline at 0/9% by weight and commonly used for priming dialyzers and extracorporeal circuits is 154 mEq/L.

The terms "dialysate flow loop," "dialysate flow path," and "dialysate conduit flow path" refers, in context, to a fluid pathway that conveys a dialysate and is configured to form at least part of a fluid circuit for hemodialysis, hemofiltration, hemodiafiltration or ultrafiltration.

The terms "dialysate regeneration unit" and "dialysate regeneration system" refer to a system for removing certain electrolytes and waste species including urea from a dialysate after contact with a dialyzer. In certain instances, the component contained within the "dialysate regeneration unit" or "dialysate regeneration system" can decrease the concentration or conductivity of at least one ionic species, or release and/or absorb at least one solute from a dialysate.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The terms "dialysis membrane," "hemodialysis membrane," "hemofiltration membrane," "hemodiafiltration membrane," "ultrafiltration membrane," and generally "membrane," refer, in context, to a semi-permeable barrier selective to allow diffusion and convection of solutes of a specific range of molecular weights through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly (methyl methacrylate), modified cellulose, or other materials known to those skilled in the art.

"Diffusive permeability" is a property of a membrane describing permeation by diffusion. Diffusion is the process of solutes moving from an area of higher concentration to an area of lower concentration.

The terms "diluate flow channel," "feed stream," "diluate stream," and the like, refer, in context, to a fluid line of solution entering an electrodialysis cell or electrodialysis unit wherein the ion concentration in the fluid solution is changed.

The terms "diluent" and "diluate" refer to a fluid having a concentration of a specific species less than a fluid to which the diluent is added.

A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode refers" to a rod electrode with a small diameter. Other electrode and electrode head geometries can be considered.

The term "disinfection fluid" refers to a solution for use in cleaning and disinfecting an apparatus for hemodialysis, hemodiafiltration or hemofiltration. The disinfection fluid may act thermally, chemically, and combinations thereof to inhibit growth of or to destroy microorganisms. The "disinfection fluid" may further act to remove, at least in part, a buildup of microorganisms on a surface of a fluid flow path, such buildups of microorganisms may be commonly referred to as a biofilm.

The terms "diverted sample stream" and "diverting a sample stream" refer redirecting part of a fluid from the main flow path to accomplish another purpose, such as to measure a fluid characteristic, remove a portion of the fluid stream in order to take a sample. More than one sample stream may be diverted, such as a "first sample stream, "second sample stream," "third sample stream," "fourth sample stream," and the like.

The term "dry" as applied to a solid or a powder contained in a cartridge means not visibly wet, and may refer interchangeably to anhydrous and also to partially hydrated forms of those materials, for example, monohydrates and dihydrates.

The term "downstream" refers to a direction in which a moving dialysate or other fluid moves within a conduit or flow path.

The term "downstream conductivity" refers to the conductivity of a fluid solution as measured at a location of a fluid flow path in the direction of the normal fluid flow from a reference point.

The term "drain connection" refers to being joined in fluid communication with a conduit or vessel that can accept fluid egress from the system.

The term "dry composition" refers to a compound that does not contain a substantial quantity of water and can include anhydrous forms as well as hydrates for example, monohydrates and dihydrates.

The term "effluent dialysate," as used herein describes the discharge or outflow after the dialysate has been used for dialysis.

The term "electrode" as used herein describes an electrical conductor used to make contact with a nonmetallic part of a circuit, such as electrical conductors used to contact the fluids of the invention (e.g. dialysate) and to measure the conductivity of the fluid.

The term "electrode" as used herein describes an electrical conductor used to make contact with a part of a fluid, a solid or solution. For example, electrical conductors can be used as electrodes to contact any fluid (e.g. dialysate) to measure the conductivity of the fluid or deliver or receive charge to the fluid. A "disc electrode" consists of an electrode with an electrode head in the shape of a disc. A "rod electrode" refers to an electrode in the shape of a rod or cylinder, with one end functioning as an electrode head. A "sheet electrode" refers to an electrode with an electrode head in the shape of a sheet. The sheet can be square, rectangular, circular or other solid planar geometries. A "mesh electrode" refers to an electrode with an electrode head consisting of a mesh, where a mesh is the same as that described for a mesh electrode. An "antenna electrode" refers to an electrode with an electrode head in the shape of an antenna, where antenna shape refers to a serpentine structure of conductive wires or strips. A "pin electrode" refers to a rod electrode with a small diameter. Other electrode and electrode head geometries can be considered.

The term "electrode array" refers to an array of one or more electrodes contained in an insulator substrate. The insulator substrate can be rigid or flexible and acts to isolate the electrodes from each other. A non-limiting example of an "electrode array" is a flex-circuit, which is a flexible circuit board containing electrodes.

The term "electrode head" refers to the portion of an electrode that is in physical contact with a fluid, that conductivity is to be measured from.

The terms "electrode rinse" and "electrode rinse solution" refer to any suitable solution such as sodium sulfate solution that prevents undesirable oxidation and flushes reactants from an electrode surface.

The terms "electrode rinse flow channel," "electrode rinse stream," and the like refer to a fluid line of an electrode rinse or "electrode rinse solution."

The term "electrode rinse reservoir" refers to a vessel or container for holding the electrode rinse or electrode rinse solution. The reservoir may have an inflexible or flexible volume capacity.

The term "electrodialysis" refers to an electrically driven membrane separation process capable of separating, purifying, and concentrating desired ions from aqueous solutions or solvents.

The term "electrodialysis cell" refers to an apparatus having alternating anion- and cation-exchange membranes that can perform electrodialysis using an electrical driving force between an anode and cathode housed at opposite ends of the cell. The cell consists of a diluate compartment fed by a diluate stream and a concentrate compartment fed by a concentrate stream. One or more electrodialysis cells can be multiply arranged to form an "electrodialysis stack."

The term "electrolyte" refers to an ion or ions dissolved in an aqueous medium, including but not limited to sodium, potassium, calcium, magnesium, acetate, bicarbonate, and chloride.

The terms "electrolyte source" and "electrolyte source" refer to a stored substance that provides one or more electrolytes.

The terms "equilibrated," "equilibrate," "to equilibrate," and the like, refer to a state where a concentration of a solute in a first fluid has become approximately equal to the concentration of that solute in the second fluid. However, the term equilibrated as used herein does not imply that the concentration of the solute in the first fluid and the second fluid have become equal. The term can also be used in reference to the process of one or more gases coming into equilibrium where the gases have equal pressures or between a liquid and a gas.

The term "equilibrated to the solute species concentration" refers to more specifically where a concentration of a particular solute species in a first fluid has become approximately equal to the concentration of that solute species in the second fluid. The concentration need not be exact.

The terms "evacuation volume," "priming volume" and "void volume" refer to the internal volume of a component or collection of components comprising a fluid flow path and are the volume of fluid that can be removed from the fluid flow path to empty the fluid flow path if it has been filled with fluid.

The term "extracorporeal," as used herein generally means situated or occurring outside the body.

The term "extracorporeal circuit" refers to a fluid pathway incorporating one or more components such as, but not limited to, conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

The term "feed solution" refers to a dialysate or ultrafiltrate fluid solution introduced into part of the dialysis or ultrafiltrate system. For example a "feed solution" can refer to a dialysate or ultrafiltrate fluid solution introduced to an electrodialysis cell.

The term "filtering media" refers to a material that can allow a fluid to pass through, but which inhibits passage of non-fluid substances that are larger than a predetermined size.

The terms "filtrate regeneration unit" and "filtrate regeneration system" refer to a system for removing certain electrolytes and waste species including urea from a filtrate produced using filtration.

The terms "filtrate regeneration circuit," "filtrate regeneration loop," and the like, refer to a flow path containing fluid resulting from filtration; for the removal of certain electrolytes and waste species including urea.

The term "filtration" refers to a process of separating solutes from a fluid, by passing the fluid through a filter medium across which certain solutes or suspensions cannot pass. Filtration is driven by the pressure difference across the membrane.

The term "first terminal end" of a flow path refers to one end of the flow path and "second terminal end" refers to another end of the flow path. Neither the "first terminal end" nor the "second terminal end" has any limitation on placement on an arterial or venous side.

The term "first terminal valve" refers to a valve substantially located at one end of a first fluid conduit without any requirement that the valve be place on an arterial or venous side. Similarly, the term "second terminal valve" refers to a valve substantially located at one end of a second fluid conduit and so on without any limitation on placement on an arterial or venous side.

The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that it recirculates, or passes the same position more than once as it moves through a flow loop. A flow loop may operate to cause fluid volume ingress to and fluid volume egress from the flow loop. The term "flow loop" and "flow path" often may be used interchangeably. Further types of flow paths may be further defined; for example, (1) a recirculation flow path, would be a flow path whose function is in whole or part is to recirculate fluid through the defined flow path; (2) a dialyzer recirculation flow path would be a flow path whose function is in whole or part is to recirculate fluid through the defined flow path having a dialyzer' (3) a controlled compliant flow path would be a flow path would be a flow path that is controlled compliant as defined herein. Any of the defined flow paths may be referred to numerically, as a first flow path, second, third flow path, or fourth flow path, and the like flow paths.

The term "flow path" refers to a route or a collection of routes for a fluid to move within. Within a flow path there may be more than one route that a fluid can follow to move from a first position to a second position. A fluid may move through a flow path such that it recirculates, or passes the same position more than once as it moves through a flow path. A flow path may be a single element such as a tube, or a flow path may be a grouping of components of any type that guide the movement of a fluid. The term "flow loop" and "flow path" often may be used interchangeably.

The terms "flow restriction," "flow restriction device" and "flow restrictor" refer to an element or grouping of elements that resist the flow of fluid through the element or grouping of elements such that the fluid pressure within a flow stream that passes through the element or grouping of elements is greater upstream of the element or grouping of elements than downstream of the element or grouping of elements. A flow restrictor may be an active or passive device. Non-limiting examples of passive flow restriction devices are orifices, venturis, a narrowing, or a simple length of tubing with flow cross section that produces the desired pressure drop when the fluid flows through it, such tubing being essentially rigid or compliant. Non-limiting examples of active flow restrictors are pinch valves, gate valves and variable orifice valves.

The term "flow stream" refers to fluid moving along a flow path

The term "fluid balance control pump" refers to where a control pump is used to adjust the concentration or amount of a solute or fluid in the system. For example, a fluid balance control pump is used for selectively metering in or selectively metering out a designated fluid wherein the concentration or amount of a solute or fluid is adjusted.

The term "fluid characteristic" refers to any chemical or biological components that make up or can be found dissolved or suspended in the fluid or gas properties associated with the fluid; or to any physical property of the fluid including, but not limited to temperature, pressure, general or specific conductivities associated with the fluid or related gases.

The term "fluid communication" refers to the ability of fluid to move from one component or compartment to another within a system or the state of being connected, such that fluid can move by pressure differences from one portion that is connected to another portion.

The term "flush reservoir" is used to describe a container that can accept or store fluid that is removed from the system during rinsing or cleaning of fluid pathways of the system, including draining the system after cleaning and/or disinfection has been completed.

"Hemodiafiltration" is a therapy that combines hemofiltration and hemodialysis.

"Hemofiltration" is a therapy in which blood is filtered across a semi-permeable membrane. Water and solutes are removed from the blood via pressure-driven convection across the membrane. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) observed in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (predilution mode, post-dilution mode).

"Hemodialysis" is a technique where blood and a "cleansing fluid" called dialysate are exposed to each other separated by a semi-permeable membrane. Solutes within the permeability range of the membrane pass while diffusing along existing concentration gradients. Water and solutes are also transferred by convection across a pressure gradient that may exist across the dialysis membrane. The dialysate employed during hemodialysis has soluble ions such as sodium, calcium and potassium ions and is not pure water. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates.

The term "hemofilter" refers to a apparatus (or may refer to a filter) used in hemofiltration. A hemofilter apparatus can be connected to an extracorporeal circuit and configured to operate with a semipermeable membrane that separates at least a portion of the fluid volume from blood to produce a filtrate fluid.

The term "hydrophobic membrane" refers to a semipermeable porous material that may allow gas phases of matter to pass through, but which substantially resists the flow of water through the material due to the surface interaction between the water and the hydrophobic material.

"Hemodiafiltration" is a therapy that combines hemofiltration and hemodialysis.

The term "in contact" as referred to herein denotes (a) a coming together or touching, as of objects or surfaces; or (b) the state or condition of touching or of being in immediate proximity. "In contact" also includes fluids that are "in fluid communication with" with a solid, such as for example, a fluid, like a dialysate, in contact with a material layer of a sorbent cartridge, or a fluid in contact with a sensor.

The terms "infusate container" and "infusate reservoir" refer to a vessel, which can be substantially inflexible or non-flexible for holding a solution of one or more salts for the adjustment of the composition of a dialysate.

The term "infusate solution" refers to a solution of one or more salts for the adjustment of the composition of a dialysate, such as salts of calcium, magnesium, potassium, and glucose.

The term "infusate system" refers to a system that incorporates at least one fluid pathway including components such as conduits, valves, pumps or fluid connection ports, an infusate container or a controller configured to add an infusate solution to the dialysate.

The term "interchangeable bicarbonate cartridge" refers to a bicarbonate cartridge that can be configured for removal and replacement with a like bicarbonate cartridge. Interchangeable bicarbonate cartridges can be single use disposable, or re-fillable, re-usable containers.

The term "interchangeable sodium chloride cartridge" refers to a sodium chloride cartridge that can be configured for removal and replacement with a like sodium chloride cartridge. Interchangeable sodium chloride cartridges can be single use disposable, or re-fillable, re-usable containers.

The terms "introduce" and "introducing" refer to causing a substance to become present where it was not present, or to cause the amount or concentration of a substance to be increased.

The term "ion-exchange material" refers to any type of resin or material that can exchange one type of ion for another. The "ion-exchange material" can include anion and cation exchange materials. In one specific case, the term can refer to the removal of ions such as potassium, magnesium, sodium, phosphate and calcium in exchange for other ions such as potassium, sodium, acetate, hydrogen and/or hydroxide.

An "ion-exchange resin" or "ion-exchange polymer" is an insoluble matrix (or support structure) that can be in the form of small (1-2 mm diameter) beads, fabricated from an organic polymer substrate. The material has a developed structure of pores on the surface of which are sites with easily trapped and released ions. The trapping of ions takes place only with simultaneous releasing of other ions; thus the process is called ion-exchange. There are multiple different types of ion-exchange resin which are fabricated to selectively prefer one or several different types of ions. In one specific case, the term can refer to the removal of ions such as potassium, magnesium, sodium, phosphate and calcium in exchange for other ions such as potassium, sodium, acetate, hydrogen and/or hydroxide.

The term "ion selective electrode" (ISE), also known as a specific ion electrode (SIE), is a transducer (or sensor) that converts the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The term "junction" refers to a common point of connection between two or more flow paths or conduits that allows a liquid and/or a gas to move from one pathway or conduit to another. A junction may be a reversible connection that can be separated when transfer of a liquid and/or gas between the flow paths or conduits is not needed.

The term "kidney replacement therapy" as used herein describes the use of a provided system to replace, supplement, or augment the function of a patient with impaired kidney function, such as would occur for a patient with Chronic Kidney Disease. Examples of kidney replacement therapy would include dialysis, hemofiltration, hemodialysis, hemodiafiltration, peritoneal dialysis, and the like.

The terms "luer connector" and "luer adapter" refer to adapters or connectors conforming to International Standards Organization (ISO) standards 594-2.

The term "manifold" refers to a collection of one or more fluid pathways that are formed within a single unit or subassembly. Many types of manifolds can be used, e.g. a cleaning and/or disinfecting manifold is used to clean or disinfect the defined flow loop when the flow loop is connected to the cleaning and/or disinfecting manifold.

The term "material layer" refers to the layers of materials found in a sorbent cartridge. The material layers in a sorbent cartridge may have one or more layers selected from a urease-containing material, alumina, zirconium phosphate, zirconium oxide, and activated carbon.

The term "memory" refers to a device for recording digital information that can be accessed by a microprocessor, such as RAM, Dynamic RAM, microprocessor cache, FLASH memory, or memory card.

The term "mesh electrode" refers to an electrode in the shape of a mesh, where a mesh consists of a planar structure with openings. The mesh can be made from; overlapping wires or strips, a sheet machined or manufactured to contain holes or openings, or a sheet with a permeable, porous structure. In all cases the mesh is manufactured from materials that result in electrodes, such as titanium, platinum, stainless steel, and iridium. In the case of an electrode mesh consisting of overlapping wires or strips, certain wires or strips can be isolated from other wires or strips with an insulator material in order to apply one polarity to certain wires or strips and the opposite polarity to other wires or strips.

The term "metabolic waste species," as used herein describes organic and inorganic components generated by a patient. They can be metabolic products such as urea, uric acid, creatinine, chlorides, inorganic sulfates and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "mid-weight uremic wastes" refers to uremic wastes that can pass through a dialysis membrane and have a molecular weight less than about 66,000 g/mol and greater than about 1000 g/mol. An example of a middle molecule is beta-2 microglobulin.

The term "mixing chamber" refers to a chamber or vessel, with one or more inlet and outlet fluid streams, that provides mixing between the fluid streams entering the chamber.

The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow loop in a controlled compliant system.

A multiplexer" or "mux" is an electronic device that selects one of several analog or digital input signals and forwards the selected input into a single line.

The term "nitrogenous waste" refers to any non-polymeric nitrogen-containing organic compound originating from the blood of a patient. Nitrogenous waste includes urea and creatinine, which are both "waste species."

The term "one-way valve" refers to a device that allows flow to pass in one direction through the valve, but prevents or substantially resists flow through the valve in the opposite direction. Such devices can include devices commonly referred to as check valves "Osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

The term "parallel or wound hollow fiber assembly" refers to any device that incorporates a porous or non-porous hollow fiber material that allows a gas to pass through the material wall of the hollow fibers, but resists the passage of a liquid through the material wall and is configured as multiple strands aligned in parallel or wrapped around a core. The liquid to be degassed may be conveyed through either the inside of the hollow fibers or around the outside of the hollow fibers. Optionally, a gas may be conveyed on the side of the material wall that is opposite the liquid to be degassed. Optionally, a vacuum may be applied on the side of the material wall that is opposite the liquid to be degassed.

A "patient" or "subject" is a member of any animal species, preferably a mammalian species, optionally a human. The subject can be an apparently healthy individual, an individual suffering from a disease, or an individual being treated for a disease.

The term "parallel to a central axis" refers to the position of components, e.g. sensors that can be placed in a plane having portions generally parallel to the central axis.

The terms "pathway," "conveyance pathway" and "flow path" refer to the route through which a fluid, such as dialysate or blood travels.

The term "patient fluid balance" refers to the amount or volume of fluid added to or removed from a subject undergoing a treatment.

The term "peristaltic pump" refers to a pump that operates by compression of a flexible conduit or tube through which the fluid to be pumped passes.

The term "perpendicular to a central axis" refers to the position of components, e.g. sensors that can be placed in a plane having portions generally perpendicular to the central axis.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient.

The term "pH-buffer modifying solution" refers to a solution that can reduce the acidity (pH) of the working dialysate solution when added to the dialysate The term "pH-buffer sensor" refers to a device for measuring the acidity or basicity (pH) and the buffer concentration of the dialysate solution.

The term "pH-buffer management system" refers to a system managing the pH and buffer concentration of a dialysate by adding, removing or generating a fluid to the dialysate such that the dialysate is modified by the pH-buffer management system to have a different pH and buffer concentration.

The term "pH-buffer measurement system" refers to a system measuring the pH and/or buffer concentration of a dialysate or fluid within the system.

The terms "portable system" and "wearable system" refers to a system in whole or in part having a mass and dimension to allow for transport by a single individual by carrying the system or wearing the system on the individual's body. The terms are to be interpreted broadly without any limitation as to size, weight, length of time carried, comfort, ease of use, and specific use by any person whether man, woman or child. The term is to be used in a general sense wherein one of ordinary skill will understand that portability as contemplated by the invention encompasses a wide range of weights, geometries, configurations and size.

The term "potable water" refers to drinking water or water that is generally safe for human consumption with low risk of immediate or long term harm. The level of safety for human consumption can depend on a particular geography where water safe for human consumption may be different from water considered safe in another jurisdiction. The term does not necessarily include water that is completely free of impurities, contaminants, pathogens or toxins. Other types of water suitable for use in the present invention can include purified, deionized, distilled, bottled drinking water, or other pre-processed water that would be understood by those of ordinary skill in the art as being suitable for use in dialysis.

The term "potassium-modified fluid" refers to fluid having a different conductivity or potassium concentration compared to a second fluid to which the potassium-modified fluid is added to modify the conductivity or potassium concentration of the second fluid.

The terms "physiologically compatible fluid" and "physiological compatible solution" refer to a fluid that can be safely introduced into the bloodstream of a living subject.

The term "plumbing," as used herein generally describes any system of valves, conduits, channels, and lines for supplying any of the fluids used in the invention.

The term "porosity," as used herein describes the fraction of open pore volume of a membrane.

The terms "pressure differential" and "pressure drop" refer to the difference in pressure measurements of a fluid between two points of measurement.

The terms "pressure meter" and "pressure sensor" refer to a device for measuring the pressure of a gas or liquid in a vessel or container.

The terms "priming process" and "priming" refer to the process of conveying a liquid into the void volume of a fluid pathway to fill the pathway with liquid.

The term "priming volume" refers to the volume of priming fluid required to fill the void volume of the subject pathway, device, or component, as the particular case may be.

The term "priming overflow reservoir" refers to a reservoir which during priming is used to collect the overflow of fluid during the priming process.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture with a stored program and being capable of carrying out a set of commands, automatically that can be changed or replaced.

The term "pump" refers to any device that causes the movement of fluids or gases by the application of suction or pressure.

The term "pulsatile pump" refers to a pump where the pumped fluid undergoes periodic variation in velocity and/or pressure.

The terms "reconstitute" and "reconstituting" refer to creating a solution by addition of a liquid to a dry material or to a solution of higher concentration to change the concentration level of the solution. A "reconstitution system" in one use, is a system that rebalances the dialysate in the system to ensure it contains the appropriate amount of electrolytes and buffer.

The terms "sorbent regeneration," "sorbent regeneration system," "sorbent system, and the like, refer, in context, to devices that are part of a sorbent regenerated dialysate delivery system for hemodialysis, functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "shunt," as most often used herein describes a passage between channels, in the described filtration and purification systems, wherein the shunt diverts or permits flow from one pathway or region to another. An alternate meaning of "shunt" can refer to a pathway or passage by which a bodily fluid (such as blood) is diverted from one channel, circulatory path, or part to another. The term "bypass" can often be used interchangeably with the term "shunt."

The term "sodium-concentrate solution" refers to a solution having a high concentration of sodium ions relative to another solution or fluid.

The terms "sodium chloride cartridge" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. For example, the sodium chloride cartridge or container can contain at least one fluid pathway and include components such as conduits, valves, filters or fluid connection ports.

The term "regenerative capacity of the sorbent" refers to the remaining capacity for the sorbent cartridge or a particular material layer of the sorbent cartridge to perform its intended function.

The term "regenerative substance" refers to a sorbent material contained in a "regeneration module." The term "first chosen regenerative substance," as used in the present invention refers to a particular regenerative substance, identified as "first chosen regenerative substance." The term "second chosen regenerative substance" refers to a particular regenerative substance, identified as "second chosen regenerative substance."

The term "regeneration module" refers to an enclosure having one or more sorbent materials for removing specific solutes from solution, such as urea. In certain embodiments, the term "regeneration module" includes configurations where at least some of the materials contained in the module do not act by mechanisms of adsorption or absorption.

The terms "remnant volume" and "residual volume" refer to the volume of fluid remaining in a fluid flow path after the fluid flow path has been partially emptied or evacuated.

The terms "replacement fluid" and "substitution fluid" refer to fluid that is delivered to the blood of a subject undergoing convective renal replacement therapies such as hemofiltration or hemodiafiltration in order to replace at least a portion of the fluid volume that is removed from the subject's blood when the blood is passed through a hemofilter or a dialyzer.

The term "reserve for bolus infusion" refers to an amount of solution available, if needed, for the purpose of administering fluid to a subject receiving therapy, for example, to treat an episode of intradialytic hypotension.

The term "reusable" refers to an item that is used more than once. Reusable does not imply infinitely durable. A reusable item may be replaced or discarded after one or more use.

The term "reverse osmosis" refers to a filtration method of forcing a solvent from a region of high solute concentration through a semipermeable membrane to a region of low solute concentration by applying a pressure in excess of osmotic pressure. To be "selective," this membrane should not allow large molecules or ions through the pores (holes), but should allow smaller components of the solution (such as the solvent) to pass freely.

The term "reverse osmosis rejection fraction" refers to the resulting solute that is retained on the pressurized side of the membrane and the pure solvent is allowed to pass to the other side in a reverse osmosis system.

The term "reversible connections" refers to any type of detachable, permanent or non-permanent connection configured for multiple uses.

The term "salination pump" refers to a pump configured to move fluid and/or control movement of fluid through a conditioning flow path, such as through or from a source of a conditioning material such as sodium chloride or sodium bicarbonate.

The term "salination valve" refers to a valve configured to control the flow of fluid in a conditioning flow path, such as through or from a source of a conditioning material such as sodium chloride or sodium bicarbonate.

The term "segment" refers to a portion of the whole, such as a portion of a fluid flow path or a portion of a fluid circuit. A segment is not limited to a tube or conduit, and includes any grouping of elements that are described for a particular segment. Use of the term "segment," by itself, does not imply reversible or detachable connection to another segment. In any embodiment, a segment may be permanently connected to one or more other segments or removably or detachably connected to one or more segments.

The terms "selectively meter fluid in" and "selectively meter fluid out" generally refer to a process for controllably transferring fluids from one fluid compartment (e.g. a selected patient fluid volume, flow path, or reservoir) to another fluid compartment. One non-limiting example is where a control pump may transfer a defined fluid volume container, reservoirs, flow paths, conduit of the controlled compliant system. When fluid is moved from a reservoir into another part of the system, the process is referred to as "selectively metering fluid in" as related to that part of the system. Similarly, one non-limiting example of removing a defined volume of dialysate from a dialysate flow path in a controlled compliant system and storing the spent dialysate in a control reservoir, can be referred to as "selectively metering-out" the fluid from the dialysate flow path.

The terms "semipermeable membrane," "selectively permeable membrane," "partially permeable membrane," and "differentially permeable membrane," refer to a membrane that will allow certain molecules or ions to pass through it by diffusion and occasionally specialized "facilitated diffusion". The rate of passage depends on the pressure, concentration, and temperature of the molecules or solutes on either side, as well as the permeability of the membrane to each solute. The term "semi-permeable membrane" can also refer to a material that inhibits the passage of larger molecular weight components of a solution while allowing passage of other components of a solution having a smaller molecular weight. For example, Dialyzer membranes come with different pore sizes. Those with smaller pore size are called "low-flux" and those with larger pore sizes are called "high-flux." Some larger molecules, such as beta-2-microglobulin, are not effectively removed with low-flux dialyzers. Because beta-2-microglobulin is a large molecule, with a molecular weight of about 11,600 daltons, it does not pass effectively through low-flux dialysis membranes.

The term "sensor," which can also be referred to as a "detector" in certain instances, as used herein can be a converter that measures a physical quantity of a matter in a solution, liquid or gas, and can convert it into a signal which can be read by an electronic instrument.

The term "sensor element" refers to a device or component of a system that detects or measures a physical property.

The terms "sodium management system" and "sodium management" broadly refer to a system or process that can maintain the sodium ion concentration of a fluid in a desired range. In certain instances, the desired range can be within a physiologically-compatible range. The sodium ion concentration of an input solution can be modified by any means including application of an electrical field.

The term "sodium-modified fluid" refers to fluid having a different conductivity or sodium concentration compared to a second fluid to which the sodium-modified fluid is added to modify the conductivity or sodium concentration of the second fluid.

The term "sodium conduit flow path" refers to a flow path in fluid communication with a sodium chloride cartridge which then can pump saturated sodium solution into the dialysate by pumping and metering action of a salination pump.

The term "sodium source" refers to a source from which sodium can be obtained. For example, the sodium source can be a solution containing sodium chloride or a dry sodium chloride composition that is hydrated by the system.

The term "solid potassium" refers to a solid composition containing a salt of potassium such as potassium chloride at any purity level. In general, the solid potassium will be easily soluble in water to form a solution.

The term "solid sodium" refers to a solid composition containing a salt of sodium such as sodium chloride at any purity level. In general, the solid potassium will be easily soluble in water to form a solution and of high purity.

The term "solid bicarbonate" refers to a composition containing a salt of bicarbonate such as sodium bicarbonate at any purity level. In general, the solid bicarbonate will be easily soluble in water to form a solution.

The term "solute" refers to a substance dissolved, suspended, or present in another substance, usually the component of a solution present in the lesser amount.

The terms "sorbent cartridge" and "sorbent container" refer to a cartridge containing one or more sorbent materials for removing specific solutes from solution, such as urea. "Sorbent cartridge" includes configurations where at least some of the materials contained in the cartridge do not act by mechanisms of adsorption or absorption.

The terms "sorbent regeneration," "sorbent regeneration system," "sorbent system, and the like, refer, in context, to devices that are part of a sorbent regenerated dialysate delivery system for hemodialysis, functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "source of cations" refers a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid. Non-limiting examples include glucose, dextrose, acetic acid and citric acid.

The term "specified gas membrane permeability" refers to a determined rate at which a gas membrane will allow a gas to pass through the membrane from a first surface to a second surface, the rate being proportional to the difference in absolute pressure of the gas in proximity to the first side of the membrane and in proximity to the second side of the membrane.

The term "spent dialysate" refers to a dialysate that has been contacted with blood through a dialysis membrane and contains one or more impurity, or waste species, or waste substance, such as urea.

The term "static mixer" refers to a device that mixes two or more component materials in a fluid solution without requiring the use of moving parts.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

The term "tap water" refers to water, as defined herein, from a piped supply.

The term "temperature sensor" refers to a device that detects or measures the degree or intensity of heat present in a substance, object, or fluid.

A "therapy solution reservoir" refers to any container or reservoir that holds a physiological compatible fluid.

The term "total bicarbonate buffer concentration" refers to the total concentration of bicarbonate ($HCO_3^-$) ion and a conjugate acid of bicarbonate in a solution or composition.

A "therapy solution reservoir" refers to any container or reservoir that holds a physiological compatible fluid.

The terms "treating" and "treatment" refer to the management and care of a patient having a pathology or condition by administration of one or more therapy contemplated by the present invention. Treating also includes administering one or more methods of the present invention or using any of the systems, devices or compositions of the present invention in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "uremic wastes" refers to a milieu of substances found in patients with end-stage renal disease, including urea, creatinine, beta-2-microglobulin.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in either a dialysis, a hemodiafiltration, or a filtration process.

The terms "unbuffered sodium bicarbonate" or "solution of unbuffered sodium bicarbonate" refer to a sodium bicarbonate composition that is not buffered with a conjugate acid or base in any amount, proportion or pH adjustment.

The term "upstream" refers to a direction opposite to the direction of travel of a moving dialysate or other fluid within a conduit or flow path.

The term "urea sensor" refers to a device for measuring or allowing for the calculation of urea content of a solution. The "urea sensor" can include devices measuring urease breakdown of urea and measurement of the resulting ammonium concentration. The sensing methods can be based on any one of conductimetric, potentiometric, thermometric, magnetoinductic, optical methods, combinations thereof and other methods known to those of skill in the art.

The term "vacuum" refers to an action that results from application of a pressure that is less than atmospheric pressure, or negative to the reference fluid or gas.

The term "vent" as referred to in relationship to a gas, refers to permitting the escape of a gas from an defined portion of the system, such as, for example, as would be found in the degassing module.

The term "void volume" refers to a specific volume that can be occupied by a fluid in a defined space such as a dialysate circuit of the invention including all components contained therein.

The terms "waste species," "waste products" and "impurity species" refers to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The term "working dialysate solution" refers to a dialysate solution that is undergoing active circulation or movement through a system including conduits, pathways, dialyzers and cartridges.

Potassium Management System

In one aspect the invention is directed toward a dialysis system having a dialysate regeneration system that employs one or more sorbent materials that release potassium ions in exchange for absorbing ammonia or ammonium ions. A potassium management system can maintain the potassium ion concentration of the dialysate in a physiological-compatible range. The potassium management system can modify the potassium ion concentration of an input solution through the application of an electric field to generate a potassium-modified fluid that has a changed potassium ion concentration greater or lesser than the dialysate. In certain embodiments, the potassium-modified fluid can have a potassium ion concentration less than the input solution provided to the potassium management system. The potassium-modified fluid can then be added to the dialysate in a dialysate flow path to modify the potassium ion concentration of the dialysate. As such, systems and methods are provided to modify the potassium ion concentration and/or conductivity of a dialysate to allow for a fixed volume of working dialysate to be regenerated to a physiological-compatible composition for hemodialysis treatment.

FIG. 1 is an example of a dialysis system having a blood path and a dialysate regeneration path separated by a dialyzer 20. The blood enters the dialyzer 20 through a flow line inlet 22 and exits through a flow line outlet 24. The dialysate regeneration circuit shown in FIG. 1 consists of a substantially inflexible volume flow loop 46, which consists of a controlled compliant dialysate flow loop as described herein. The dialysate solution is recirculated with a dialysate pump 30 and allowed to flow through a dialysate regeneration unit 32 and a potassium management system 38.

The dialysate regeneration unit 32 or filtrate regeneration unit 33 contains components or materials that are capable of removing solutes from the dialysate including: urea, phosphate, calcium, magnesium, sodium, creatinine, uric acid, beta-2-microglobulin and sulfate among others. The dialysate regeneration unit 32 or filtrate regeneration unit 33 may also contain components or materials that release or bind potassium during the process of removing solutes from the dialysate. For example, the dialysate regeneration unit 32 or filtrate regeneration unit 33 may consist of a sorbent cartridge containing activated carbon, urease, zirconium phosphate and hydrous zirconium oxide, similar to the sorbent cartridge used in the "REDY" system known to those of skill in the art. However, any materials that have cation exchange properties, such as zirconium phosphate, are saturated or substantially saturated with potassium unlike the sorbents of the "REDY" system. As such, cations in a spent dialysate or filtrate eluting from the dialyzer 20 or the hemofilter 101 of FIG. 9 such as calcium, magnesium, sodium, ammonia/ammonium, are absorbed by such cation exchange materials with potassium ions released from the cation exchange materials to allow for charge balance within the dialysate passing through the dialysate regeneration unit 32 or the filtrate passing through the filtrate regeneration unit 33.

The dialysate exiting the dialysate regeneration unit 32 flows through a potassium management system 38 and a by-pass loop 36, regulated by a by-pass regulator 34. The by-pass regulator 34 determines the amount of dialysate that passes through the potassium management system 38. The by-pass regulator 34 could consist of a pinch valve, on/off valve, or a valve with a range of open conditions such as a needle valve. The potassium management system 38 acts to remove or add potassium to the dialysate. The potassium management system 38 and by-pass loop 36 can be placed at any one of several locations along the dialysate flow loop 46, but preferably immediately after the dialysate regeneration unit 32. In certain embodiments the use of the by-pass loop 36 is not necessary if the potassium management system 38 actively controls the amount of potassium modification performed. Active control may include monitoring potassium concentration prior to entering the potassium management system 38 using any of the monitoring means described herein and known to those of skill in the art. For example, in certain embodiments removal of the by-pass loop 36 in FIG. 1 or closing valve 34 will result in all of the dialysate flowing through the potassium management system 38. The potassium management system 38 can adjust the amount of potassium added or removed from the dialysate based on system needs as described herein to maintain acceptable levels of potassium concentration.

In certain embodiments, the potassium management system 38 is placed in a location between the dialysate regeneration unit 32 and the dialyzer 20. Because the dialysate regeneration unit 32 removes waste species from the dialysate, including urea and electrolytes, the potassium management system acts mainly on the removal or modification of potassium. In certain embodiments, a deionization resin or material or cartridge is located upstream from the dialysate regeneration unit 32 and downstream from the dialyzer 20. However, the deionization resin or material or cartridge can be located at any location on the circuit suitable for removing sodium and other electrolytes prior to entering the dialysate regeneration unit 32. As shown in FIG. 1, part of the dialysate in the dialysate flow loop 46 can be diverted through the deionization cartridge 51 and controlled by valve 50 prior to reaching the dialysate regeneration unit 32 or the potassium modification system 38. In certain embodiments, a flow restrictor (not shown) having substantially greater resistance to flow than cartridge 51 can cause fluid to flow to the cartridge 51. In other embodiments, a control valve (now shown) can be plumbed in parallel to cartridge 51 to provide for flow through same. During certain modes of operation, valve 50 can be shut to avoid flow through deionization cartridge 51. The deionization cartridge 51 can by employed with any embodiment described herein. The deionization material or cartridge can be a mix of cation and anion exchange resins that substantially removes sodium and other electrolytes from the dialysate prior to the dialysate reaching the dialysate regeneration unit 32. As such, the potassium management system can primarily operate on the modification of potassium as described above. Therefore, the size and power requirements for the potassium management system can be minimized.

After passing through the potassium management system 38 or by-pass loop 36 the dialysate flows passed a potassium sensor or conductivity sensor 40 shown in FIG. 1 As used herein, a potassium sensor refers to a device that gives an indication of potassium ion concentration or an indication of overall conductivity of a fluid or solution. Where potassium is the principle cation present in the dialysate, conductivity gives a direct indication of potassium concentration. The potassium sensor 40 measures the amount of potassium in the dialysate at that point and can be used to control the operation of the potassium management system and the by-pass regulator 34. The potassium sensor 40 can consist of an ion-selective electrode, conductivity monitor, or any other suitable sensor technology for measuring potassium in aqueous solutions known to those of skill in the art. The potassium sensor 40 may optionally also be connected anywhere along the dialysate flow loop 46; however, in certain embodiments the potassium sensor 40 is located between the potassium management system 38 and the dialyzer 20 and/or between the dialysate regeneration unit 32 and the potassium management system 38.

Blood circulating through the dialyzer 20 via an extracorporeal circuit or blood path exchanges waste components with dialysate circulating through the dialyzer 20 and dialysate flow loop 46. Waste species including ions and uremic toxins, such as uric acid, creatinine, and β2-microglobin, and urea diffuse from the blood to the dialysate within the dialyzer 20 via a semipermeable membrane contained therein.

Regeneration of the dialysate within the dialysate flow loop 46 can be achieved through contacting the dialysate with sorbents contained within the dialysate generation unit 32. Examples of useful sorbent materials include the REDY sorbent system and U.S. Pat. Nos. 3,669,880; 3,989,622; 4,581, 141; 4,460,555; 4,650,587; 3,850,835; 6,627,164; 6,818,196; and 7,566,432 and U.S. Patent Publications 2010/007838; 2010/0084330; and 2010/0078381 and International Patent Publication WO 2009/157877 A1, which are incorporated herein by reference. As discussed above, the sorbents are prepared to be saturated or substantially saturated with potassium ions as an ion for cation exchange. In some embodiments, the dialysate regeneration unit 32 can contain at least three or four different kinds of materials as follows: 1) a urease-containing material, where urease is an enzyme that catalyzes the conversion of urea to ammonium ions and carbon dioxide; 2) a zirconium phosphate (ZrP) material that has the capacity to act as a cation exchanger by absorbing a large quantity of ammonium ions in exchange for potassium and hydrogen ions; 3) a zirconium oxide material (ZrO),), namely hydrous zirconium oxide, which acts as an anion exchanger by exchanging phosphate for acetate; and 4) an activated carbon material that has a surface area for adsorption of wide range of impurities including metal ions and uremic toxins, such as uric acid, creatinine, and β2-microglobin. However, there is no limitation on the minimum number of kinds of materials used in the dialysate regeneration unit 32 wherein the unit can contain any one or two of the materials disclosed herein. In some embodiments, the zirconium phosphate material can be replaced with a magnesium phosphate material.

The principal waste species removed during hemodialysis treatment of a patient is urea that accumulates in the blood of individuals with various degrees of kidney disease or impairment. Since urea is an electrically neutral species, the dialysate regeneration unit 32 or filtrate regeneration unit 33 can convert urea to a charged ammonium species that can then be removed from the dialysate before the dialysate exits the regeneration unit 32. In certain embodiments, the ammonium may be removed by an ion exchange material prior to exiting the dialysate regeneration unit 32. However, in order to maintain electrical neutrality, the removal of charged ammonium species is matched by exchange with another charged species, which is potassium ion in certain embodiments. Materials that perform a similar exchange using sodium ions are known; however, a continuous increase in sodium ion concentration in the dialysate can occur during treatment requiring periodic adjustment of the dialysate. Since a significant concentration of sodium ions is present in the dialysate to maintain physiological compatibility, a partial adjustment of the sodium ion concentration needs to be judged in such systems. The use of potassium as the ion for exchange with urea within the dialysate regeneration unit 32 allows for the amount of potassium ions that needs to be removed from the dialysate eluting from the dialysate regeneration unit 32 to be controlled, for example, by modification of the flow rate of dialysate through the dialysate regeneration unit 32. As such, the concentration of potassium ions can increase over time.

As further shown in FIG. 1, after the potassium sensor 40, the dialysate flow passes a reconstitution system 43 consisting of an infusate pump 42 and an infusate reservoir 44. The reconstitution system 43 rebalances the dialysate to ensure it contains the appropriate amount of electrolytes and buffer. The infusate reservoir 44 may contain multiple reservoirs each containing specific compounds. For example, the infusate reservoir 44 can consist of a reservoir containing a concentrated electrolyte solution such as calcium acetate, magnesium acetate, potassium acetate and concentrated acid solution such as acetic acid or citric acid. The infusate reservoir 44 can also consist of an additional reservoir containing a concentrated buffer solution such as sodium bicarbonate, sodium lactate and/or sodium chloride to replenish the sodium ion concentration of the dialysate needed for physiological compatibility. Multiple reconstitution systems 43 can be used with the dialysis system shown in FIG. 1.

Regenerated dialysate 25 passes through the dialyzer 20 and exits the dialyzer 20 as waste or spent dialysate 23. The waste dialysate 23 flow passes an ultrafiltration unit that consists of an ultrafiltration or control pump 28 and ultrafiltration reservoir 26. The ultrafiltration pump 28 removes fluid from the dialysate loop 46 and, because of the dialysate loop's 46 substantially inflexible volume or controlled compliant properties, fluid is drawn across dialyzer 20 from the blood. The ultrafiltrate system acts to remove ultrafiltrate from the patient and remove any fluid volume added in along the dialysate loop 46, such as fluid from the reconstitution system 43. The fluid removed by ultrafiltrate pump 28 is collected in the ultrafiltrate reservoir 26.

In certain embodiments, the components of the dialysate flow loop 46 have a controlled compliant dialysate loop. As such, fluid is in passive equilibrium from flowing from the extracorporeal circuit or blood path to the dialysate flow loop 46 due to the controlled compliant volume of the dialysate loop 46. The net balance of fluid is prevented from passively flowing between the flow loop 46 to the extracorporeal circuit via the dialyzer 20 since such a movement of fluid will leave a vacuum in the flow loop 46 or require the flow loop 46 to expand. Since the dialyzer can be a high-flux type that readily allows for the passage of water, there is some fluid flux back and forth across the dialyzer membrane due to the pressure differential on the blood and dialysate sides of the membrane. This is a localized phenomenon due to the low pressure required to move solution across the membrane and is called backfiltration, however, this results in no net fluid gain or loss by the patient.

In any embodiment of the invention, the components forming the dialysate flow loop 46 can have a controlled compliant volume such that the dialysate flow loop 46 further incorporates a control or ultrafiltration pump 28 that can be operated bi-directionally to cause the movement of fluid from an extracorporeal side of the dialyzer 20 into the dialysis flow loop 46 or to cause net movement of fluid from the dialysate flow loop 46 into the extracorporeal side of the dialyzer 20. Specifically, the control or ultrafiltration pump 28 can be operated in the efflux direction to cause the movement of fluid from the extracorporeal side of the dialyzer 20 into the dialysis flow loop 46 and in the influx direction to cause the movement of fluid from the dialysis flow loop 46 into the extracorporeal side of the dialyzer 20. The action of typical pumps contemplated by the invention can function by expanding or contracting a space wherein any suitable type can be used in the present invention.

In certain embodiments, operation of the control or ultrafiltration pump 28 in the influx direction can be substituted with operation of the infusate pump 42 to drive liquid from the infusate reservoir 44 into the dialysis flow loop 46 and subsequently cause movement of fluid from the dialysis flow loop 46 to the extracorporeal side of the dialyzer 20. The control or ultrafiltration pump 28 can also be used for the movement of fluid in the opposite direction across the dialyzer 20 into the dialysis flow loop 46. It is noted that the infusate reservoir 44 or ultrafiltrate reservoir 26 can allow the system to adjust the patient fluid volume by withdrawing fluid and storing the desired amount in the respective reservoir and/or by providing rebalanced fluids to the patient and removing waste products. For example, the fluid stored in a control reservoir attached to the dialysate circuit can be used to store a volume of fluid equal to the ultrafiltrate volume removed from the patient during ultrafiltration (UF). Alternatively, the fluid stored in the control reservoir can be an infusate delivered to the patient. In certain embodiments, the delivered fluid can contain a therapeutic component deliverable across the dialyzer 20 and into the patient's bloodstream. Additionally, the volume of the dialysate flow loop 46 can be actively controlled by the user or a programmed controller.

The control or ultrafiltration pump 28 allows for fluid to move from the dialysate flow loop 46 to the extracorporeal side without creating a vacuum, wherein the operation of the control pump 28 is controlled as described herein. Likewise, the control pump 28 allows for fluid to move from the extracorporeal side, and hence the patient's body via the action of the control pump 28 as described herein. Movement of fluid between the extracorporeal side of the dialyzer 20 and the dialysate flow loop 46 can be accurately controlled and metered using the removed fluid in certain embodiments. In other embodiments, the removed fluid can be transferred back to the patient through dialysate flow loop 46 using ultrafiltrate stored in the ultrafiltrate reservoir 26. In some embodiments, the ultrafiltrate reservoir 26 can be prefilled with water, dialysate or other fluid for addition to the dialysate flow loop 46 and/or for use or treatment within the potassium control system 38.

As such, some embodiments have a controlled compliant dialysate flow loop 46 that can be accurately controlled to precisely remove or add fluid to the extracorporeal side of the dialyzer 20. Due to the substantially inflexible void volume of the conduits, the dialysate regeneration unit 32 and other components of the dialysate flow loop 46, the net movement of fluid over any time interval across the dialysate membrane within the dialyzer 20 can be accurately controlled by creating a means to accurately introduce or remove fluid from the patient. This capability can further be used to enhance the convective clearance of the system for uremic impurities while controlling the net fluid removed from the patient, for example, creating periods of fluid movement across the membrane with occasional reversal of direction to remove waste species by solvent drag. However, the present invention is not limited to a controlled compliant flow path. As such, the dialysate flow loop 46 in certain embodiments is not a controlled compliant flow path and may include one or more open reservoirs for storing or accumulating dialysate.

In certain embodiments, a control or ultrafiltration pump 28 can be a peristaltic pump, a volumetric metering pump, diaphragm pump, or a syringe style pump. Hence, the dialysate flow loop 46 has a substantially inflexible volume that can deliver controlled changes in fluid to the patient modulated by the control or ultrafiltration pump 28, or the infusate pump 42 or optionally any other pump(s) that add or remove fluid to and from the dialysate flow loop 46. The contents of U.S. patent application Ser. No. 13/565,733 filed on Aug. 2, 2012 are incorporated herein by reference in their totality.

In certain embodiments, the dialysate flow loop 46 has a void volume from about 0.15 L to about 0.5 L. In other embodiments, the dialysate flow loop 46 has a void volume from about 0.2 L to about 0.4 L or from 0.2 L to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 L to about 5 L, and micro-volumes from as small as 0.1 L to about 0.5 L such as 0.1 L to 0.2 L, 0.1 L to 0.3 L, 0.1 L to 0.4 L, 0.2 L to 0.3 L, 0.3 L to 0.4 L, or 0.3 L to 0.5 L are contemplated by the invention.

Configuration of Potassium Management System

Figure 2:
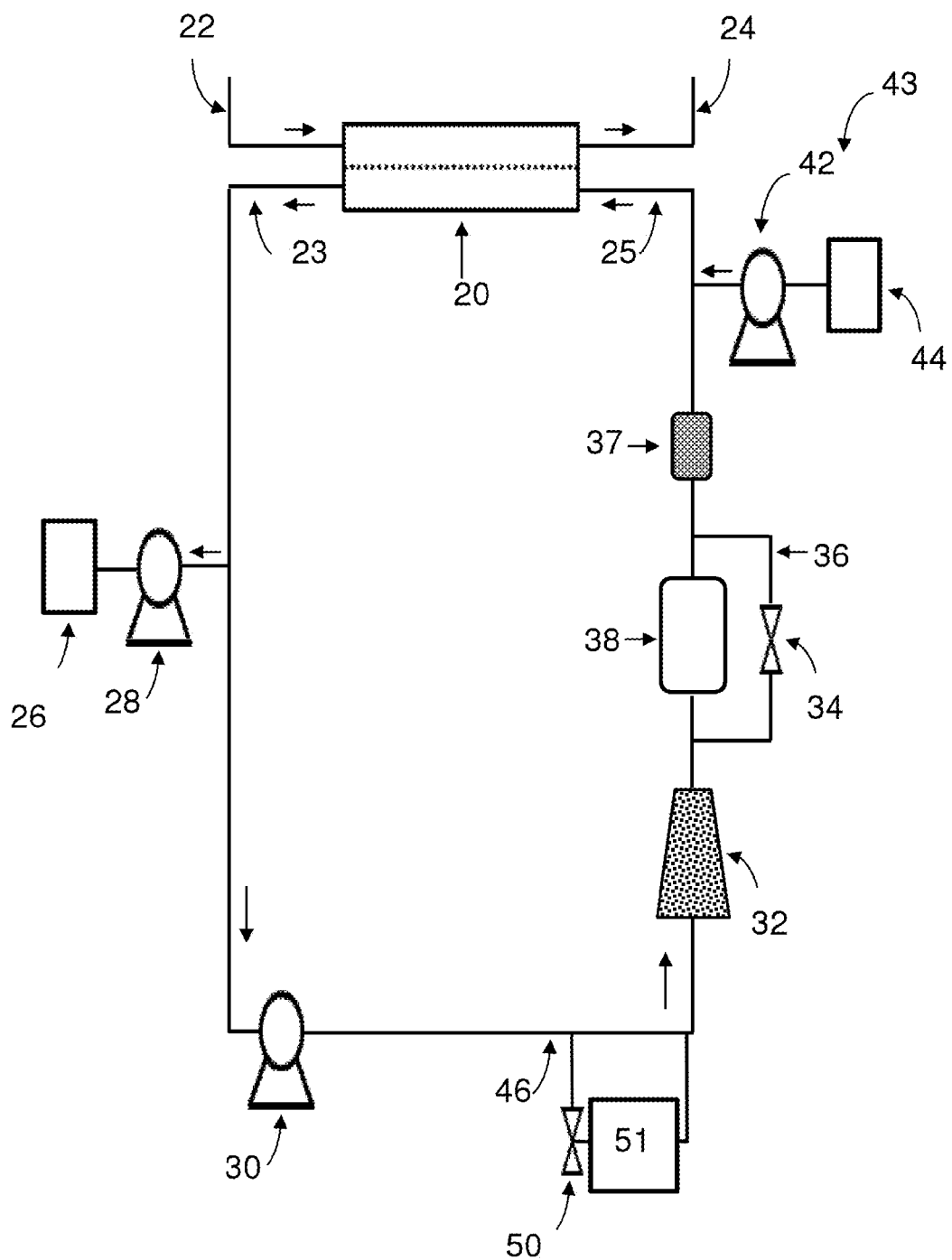
FIG. 2 is a flow diagram of a dialysate regeneration system with a controlled compliant dialysate circuit containing both a potassium management system and a potassium removal cartridge.

FIG. 2 is an example of a dialysis system similar to that shown in FIG. 1. However, the potassium sensor 40 is optionally not required. The dialysate exiting the potassium management system 38 is passed through a potassium removing sorbent cartridge 37 containing a cation exchange resin to remove any remaining potassium in the dialysate. The cation exchange resin could include zirconium phosphate. In some cases the zirconium phosphate could be in the sodium form. Because the dialysate concentration of potassium exiting the potassium management system 38 will be low, a minimal amount of sodium will be released in exchange for potassium. Therefore, additional methods to manage the released sodium are not necessary. After the potassium removing sorbent cartridge 37, the dialysate flows to the reconstitution system 43 as described above in FIG. 1. The ultrafiltrate reservoir 26 of either FIG. 1 or 2 can optionally hold a small volume of fluid that can be used for system priming, dialysis therapy, provision of fluid bolus, blood rinse back and system cleaning and disinfection via pump 28.

Figure 3:
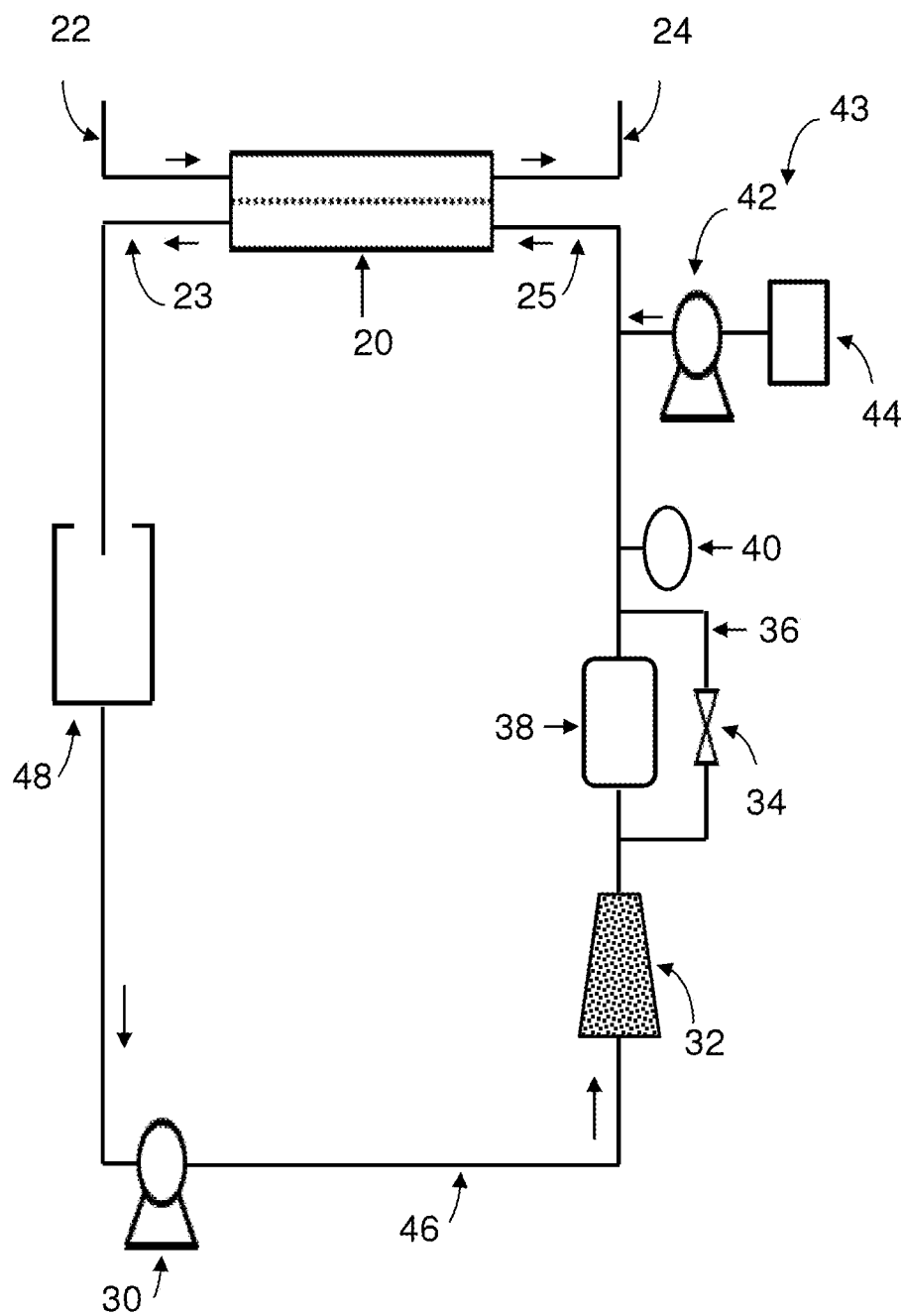
FIG. 3 is a flow diagram of a dialysate regeneration system with an open, non-fixed volume dialysate circuit and a potassium management system.

FIG. 3 is an example of a dialysis system similar to that shown in FIG. 1. However, the dialysate flow loop 46 shown in FIG. 3 includes a dialysate reservoir 48. Dialysate reservoir 48 is a variable volume reservoir. The dialysate fluid contained in dialysate reservoir 48 can vary during the course of a hemodialysis run. Specifically, the volume will increase as ultrafiltrate is removed from the patient by filtration across dialyzer 20. Control of net ultrafiltration may be accomplished by a variety of means known in the art, such as balance chambers and an ultrafiltration (UF) metering pump, duplex metering pumps and a UF metering pump, and transmembrane pressure regulators with mass or volume measurement (not shown). As used herein, the term ultrafiltrate includes fluid contained in the dialysate reservoir 48.

Figure 4:
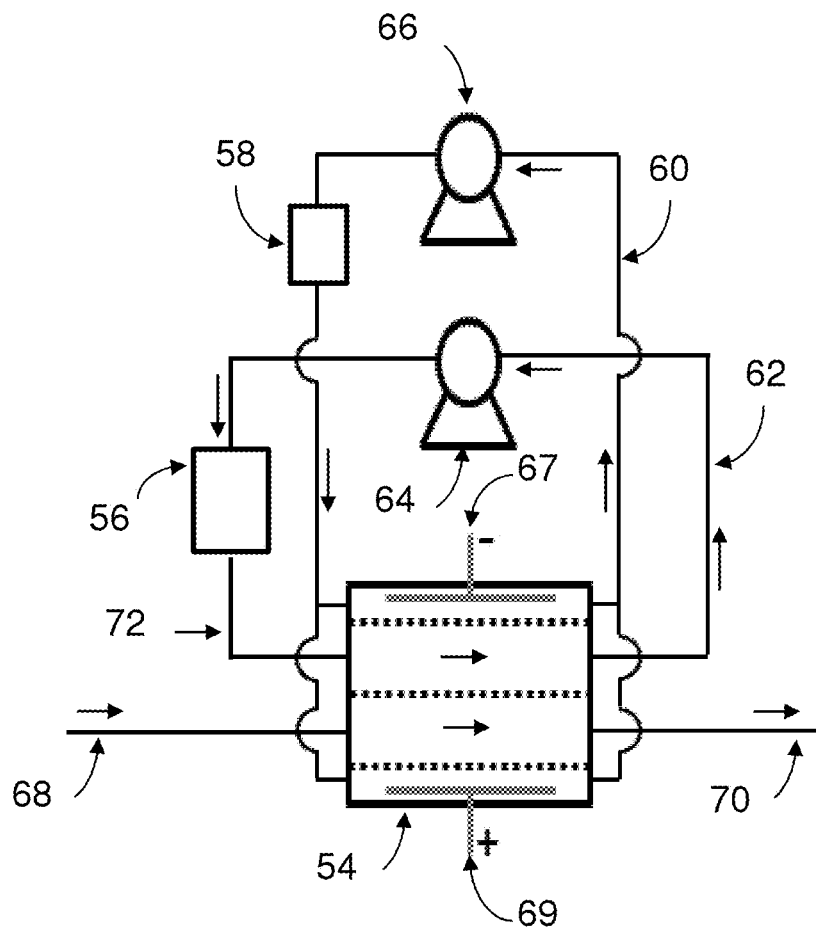
FIG. 4 is a flow diagram of a potassium management system consisting of an electrodialysis cell with concentrate and electrode rinse flow loops and dialysate inlet and outlet diluate streams.

FIG. 4 shows a flow diagram for an electrodialysis system that can function as the potassium management system identified as 38 in FIGS. 1 and 3. The diluate inlet 68 to the electrodialysis system can be in fluid communication with dialysate from the flow loop 46 or with ultrafiltrate. The dialysate or ultrafiltrate enters the electrodialysis system at the diluate inlet 68 and passes through an electrodialysis cell 54. The electrodialysis cell 54 consists of a stack of alternating cation and anion exchange membranes. In alternative embodiments, the electrodialysis cell 54 can contain a stack of bipolar and cation exchange membranes to result in alternating flow channels through the electrodialysis cell 54 (not shown). In particular, the bipolar membrane has an anion exchange membrane and a cation exchange membrane bonded together. Examples of bipolar membranes and cation exchange membranes that could be used include Neosepta BP-1E bipolar membrane and Neosepta CMX cation exchange membrane produced by ASTOM Corporation. The cation exchange membrane is designed to only allow cations to pass through it. The bipolar membrane is designed to not allow cations and anions to pass through it. Upon entering the electrodialysis cell 54, the dialysate or ultrafiltrate passes through certain flow channels that are acidified during operation (not shown).

At each end of the membrane stack is an electrode 67 and 69 contained in an electrode compartment. The electrode compartment is continually rinsed during operation with an electrode rinse solution contained in the electrode rinse reservoir 58 and recirculated with the electrode rinse pump 66. The electrode rinse solution may consist of a potassium sulfate or sodium sulfate solution, or any other suitable electrode rinse solution. The use of potassium sulfate is preferred because oxidation of sulfate does not occur to an appreciable amount under normal typical operating conditions of 1 to 2 volts per cell pair. The use of potassium chloride in the electrode rinse must be avoided to prevent the oxidation of chloride to chlorine at the electrodes, which may diffuse into the diluate stream and contaminate the dialysate. The electrode rinse acts to continually flush reactants that may form at the electrode surfaces. For example, the electrolysis of water will occur to some extent at the electrodes resulting in the formation of hydrogen and oxygen. In some embodiments, a degassing module can be included in the electrode rinse circuit to remove some of the formed gases. The degassing module can consist of a hydrophobic membrane vent. The alternating stack of anion and cation exchange membranes results in alternating flow channels through the electrodialysis cell 54. The dialysate passes through certain flow channels separated from another solution passing through the alternating flow channels. The solution referred to as concentrate is contained in the concentrate reservoir 56 and recirculated through the electrodialysis cell 54 with the concentrate pump 64. The concentrate solution may initially be water or a potassium chloride solution, or any other suitable solution known to those of skill in the art.

During operation, the electrodialysis system illustrated in FIG. 4 works by passing the dialysate or solution into the electrodialysis cell 54 through the diluate inlet 68 while recirculating the electrode rinse 58 and concentrate 56 solutions. In order to achieve potassium removal from the dialysate or ultrafiltrate waste entering the electrodialysis cell 54, a voltage is applied across the electrodes 67 and 69 to promote movement of potassium ions from the diluate stream to the concentrate stream. In order to increase the potassium concentration of the dialysate or ultrafiltrate waste entering the electrodialysis cell 54, the voltage applied is reversed across the electrodes 67 and 69.

Figure 5:
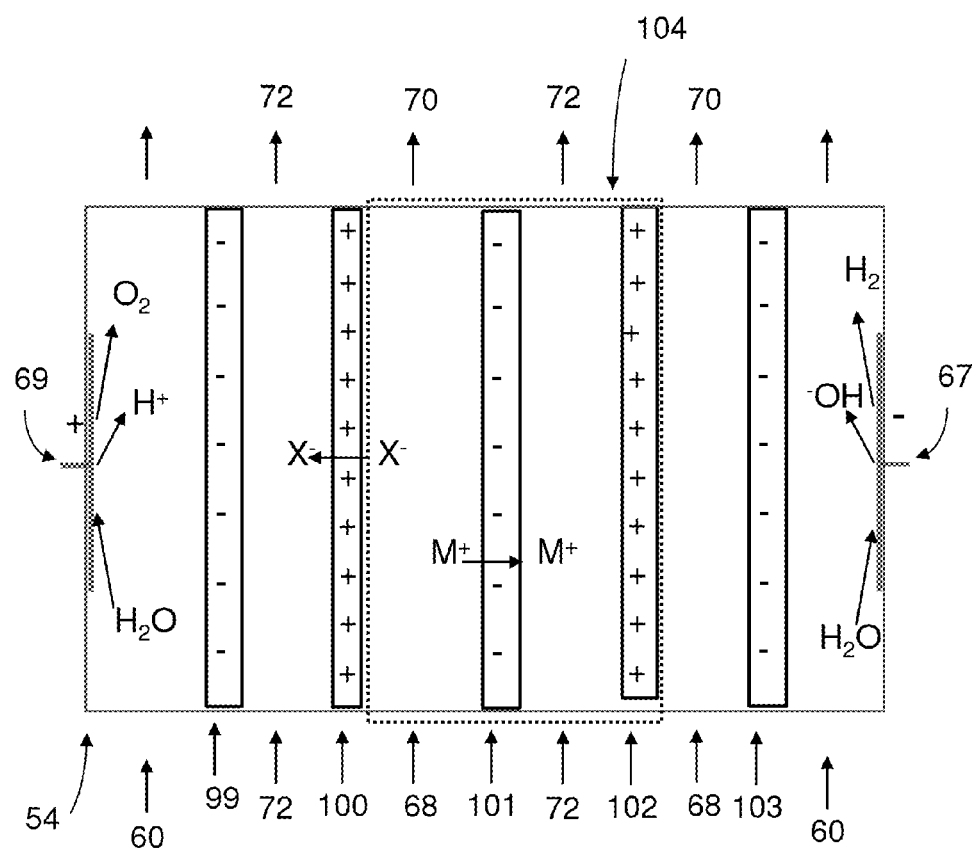
FIG. 5 is a flow diagram of an electrodialysis cell.

FIG. 5 shows a flow diagram detailing the electrodialysis cell 54. A diluate stream 68 enters the electrodialysis cell 54 between a cation exchange membrane 101 depicted in FIG. 5 and an anion exchange membrane 100. When a potential is applied across the electrodes 67 and 69, anions (X−) are drawn towards the anode 69 and flow through the anion exchange membrane 100. Cations (M+) are drawn towards the cathode 67 and flow through the cation exchange membrane 101. The anions and cations are collected in separate flow streams known as concentrate streams 72. The dashed line in FIG. 5 highlights a single stack, or cell 104 contained in the electrodialysis cell 54. Multiple cells can be stacked together in the configuration shown of alternating cation and anion exchange membranes. Multiple cells will result in multiple diluate 68 and concentrate 72 streams entering the electrodialysis cell 54, which are recombined upon exiting the electrodialysis cell 54. Shown in FIG. 5 are the electrode rinse streams 60 flowing past the anode 69 and cathode 67. A common electrode reaction that results is the electrolysis of water with the side products illustrated. The electrode rinse 60 acts to sweep these side products away from the electrodes in order to maximize current efficiency in the electrodialysis cell 54. The electrode rinse streams 60 from the anode 69 and cathode 67 are preferably combined, as illustrated in FIG. 4, in order to neutralize any hydrogen and hydroxyl ions formed. Finally, the placement of cation exchange membranes 99 and 103 next to the electrodes prevents the transport of chloride into the anode 69 compartment. Chloride is easily oxidized to chlorine at the anode and if formed could cause harm to the patient. The cation and anion exchange membranes can be any commercially available cation and anion exchange membranes, such as Neosepta CMX and Neosepta AMX, respectively, produced by ASTOM Corporation (Japan). The electrodes can be made from any suitable material including platinum, iridium, carbon, titanium, steel, or other materials known to those skilled in the art.

Figure 6:
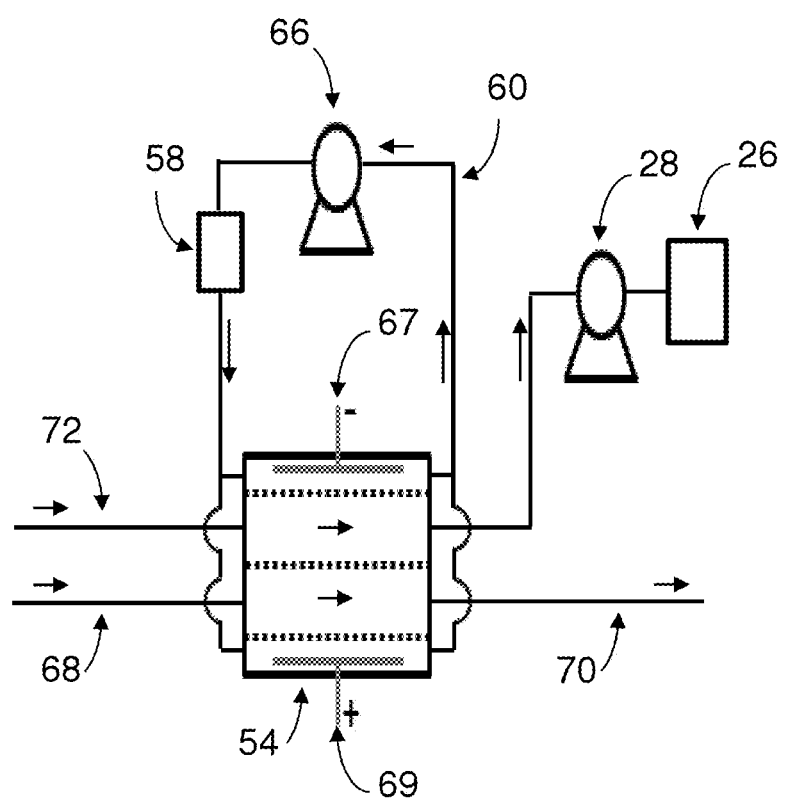
FIG. 6 is a flow diagram of a potassium management system consisting of an electrodialysis cell with an electrode rinse flow loop, dialysate inlet and outlet diluate streams and ultrafiltrate waste inlet and outlet concentrate streams.

FIG. 6 shows a flow diagram for an electrodialysis system that can be utilized in FIGS. 1, 2 and 3 as a potassium management system 38. The operation is the same as that described for the system shown in FIG. 4, except the ultrafiltrate waste or dialysate from the dialysate reservoir 48 is utilized as the concentrate solution. As shown in FIG. 6 the concentrate solution 72 passes through the electrodialysis cell 54 by being drawn with the ultrafiltrate pump 28 and collected in the ultrafiltrate reservoir 26. Utilization of the ultrafiltrate waste or dialysate from the dialysate reservoir 48 minimizes the amount of fluid necessary to operate the system.

Figure 7:
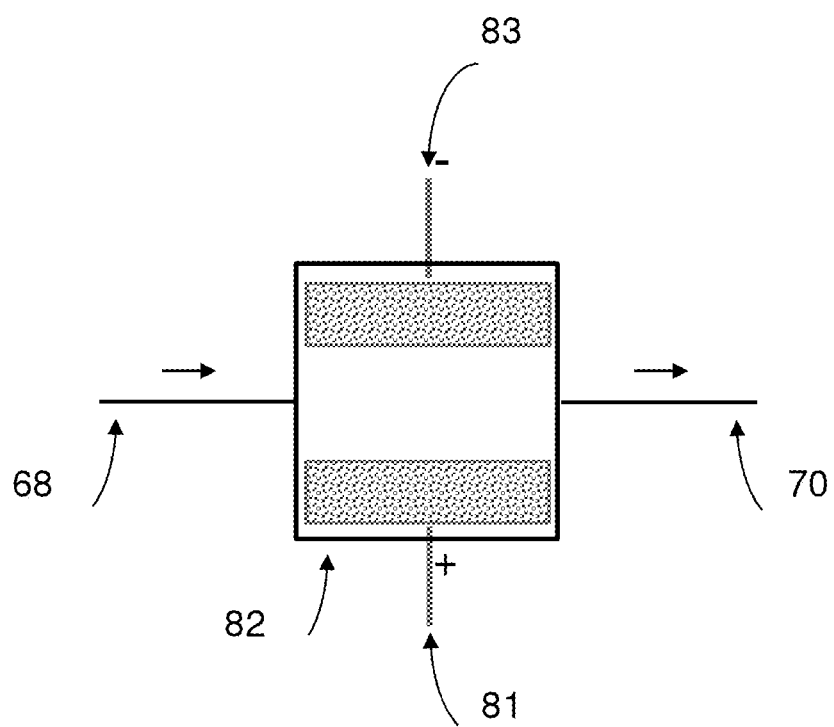
FIG. 7 is a flow diagram of a potassium management system consisting of a capacitive deionization unit and dialysate inlet and outlet streams.

FIG. 7 shows a flow diagram for a capacitive deionization system that can function as the potassium management system identified as 38 in FIGS. 1, 2 and 3. The diluate inlet 68 to the capacitive deionization system can consist of dialysate. The dialysate enters the capacitive deionization system at the diluate inlet 68 and passes through a capacitive deionization cell 82. The capacitive deionization cell 82 can have at least two electrodes 81 and 83 at each end. The electrodes may be carbon or other suitable material. When a voltage is applied across the electrodes, ions in the dialysate waste will be drawn to the electrodes, resulting in an outlet stream 70 that will have a lower concentration of ions, namely potassium and its counter ions. Non-ionic species such as urea will not be affected by the capacitive deionization system. The capacitive deionization cell may contain several electrode pairs stacked in parallel to increase the total electrode surface area and ultimately the capacity to remove potassium ions from the dialysate stream. The capacitive deionization system can also be used to increase the potassium concentration of the dialysate by reversing the polarity of the electrodes for a period of time or reducing the voltage across the electrodes to zero for a period of time. This will act to force potassium ions off of the electrodes into the dialysate or ultrafiltrate stream.

Figure 8:
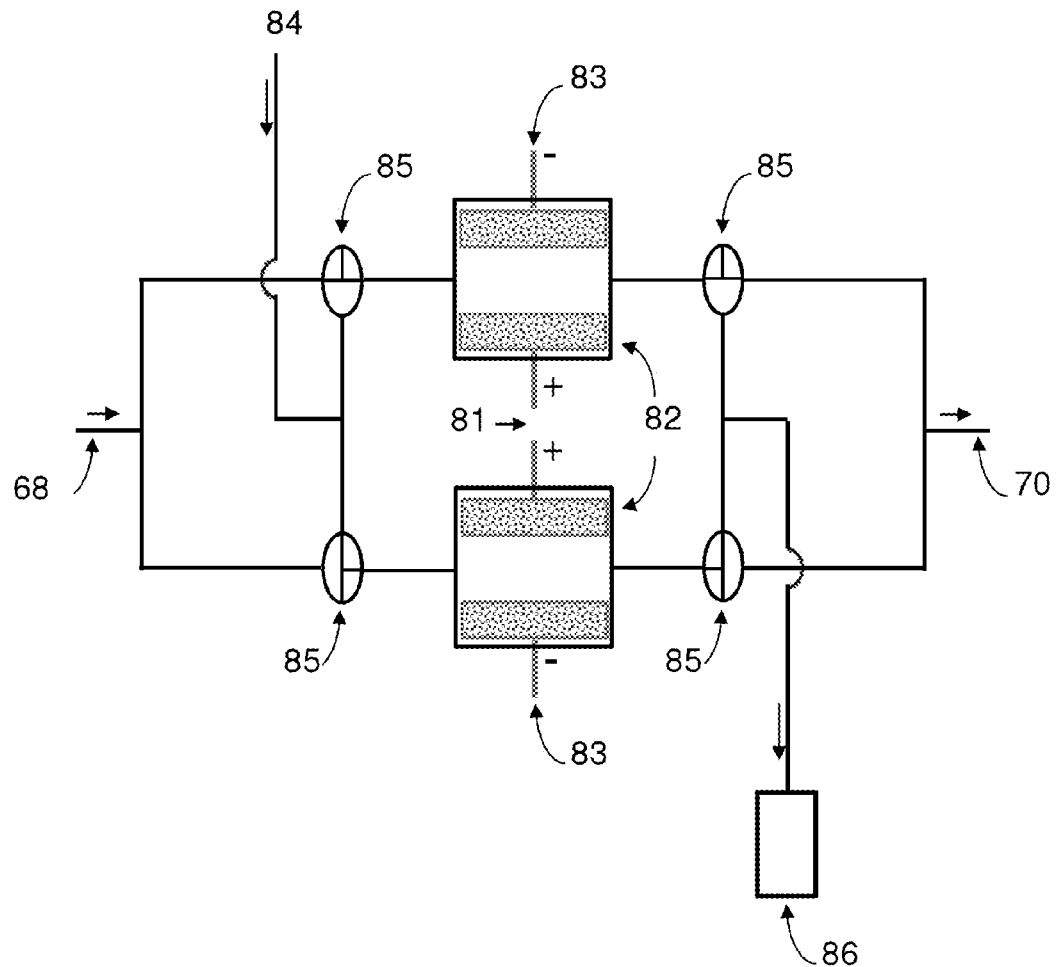
FIG. 8 is a flow diagram of a potassium management system consisting of two capacitive deionization units, a flow path for a flushing fluid and dialysate inlet and outlet streams.

FIG. 8 shows a flow diagram for a capacitive deionization system that can function as the potassium management system identified as 38 in FIGS. 1, 2 and 3. The diluate inlet 68 to the capacitive deionization system can consist of dialysate or ultrafiltrate. The dialysate or ultrafiltrate enters the capacitive deionization system at the diluate inlet 68 and passes through one of two capacitive deionization cells 82. The capacitive deionization cells 82 can have at least two electrodes 81 and 83 at each end. The electrodes may consist of carbon or other suitable material. When a voltage is applied across the electrodes, ions in the dialysate or ultrafiltrate waste will be drawn to the electrodes, resulting in an outlet stream 70 that will have a lower concentration of ions, namely potassium and its counter ions. The capacitive deionization cells 82 can contain several electrode pairs stacked in parallel to increase the total electrode surface area and ultimately the capacity to remove potassium ions from the dialysate or ultrafiltrate waste streams. The presence of two capacitive deionization cells 82 allows one cell to be regenerated while the other cell is removing potassium ions. A flushing flow stream 84 can enter either cell depending on the placement of four three-way valves 85. Other placement options for the three-way valves 85 to accomplish the same flow control function are possible and can be envisioned by those of skill in the art. The valves can also be used to determine which capacitive deionization cell 82 the dialysate or ultrafiltrate waste enters. FIG. 8 shows the appropriate valve positions for the flushing fluid 84 to pass through a bottom cell and the dialysate fluid 68 to pass through a top cell. The flushing fluid may consist of ultrafiltrate waste, water from an additional reservoir, or a cleaning solution such as potassium or sodium citrate. The capacitive deionization cell 82 can be regenerated using a flushing fluid by temporarily reversing the polarity of the electrodes to force the ions off and then by reducing the voltage across the electrodes to zero to prevent re-binding of ions in the flushing solution. After passing through the cell, the flushing solution is collected in a reservoir 86. The method of using two capacitive deionization cells allows for continual regeneration during a hemodialysis run, which will minimize the surface area requirements of the electrodes and reduce the overall system size. The capacitive deionization system may also be used to increase the potassium concentration of the dialysate by reversing the polarity of the electrodes for a period of time or reducing the voltage across the electrodes to zero for a period of time. This will act to force potassium ions off of the electrodes into the dialysate or ultrafiltrate stream. The single unit capacitive deionization system shown in FIG. 7 could also operate in a flushing mode for regeneration of the electrodes. For example, if a three-way valve (not shown) is placed along the outlet steam 70 with an additional flow path to a waste reservoir, periodically the dialysate could be diverted to the waste reservoir to flush the electrodes. The method of reversing the polarity during the flushing process would maximize the regeneration of the electrodes and minimize the amount of dialysate fluid required.

EXAMPLE

Electrodialysis for Potassium Management

Potassium generated from an ion-exchange based dialysate regeneration system can be removed or adjusted using electrodialysis. Assuming a 5 day/week hemodialysis schedule with a 70-kg patient generating BUN at a rate of 63 grams/week. The amount of urea to be removed from the dialysate per session will be 470 millimoles. Normal blood serum potassium ion concentration is from 3.5 to 5.0 mmol/L. As such, this concentration of potassium ion may be left in the dialysate for use in the dialyzer upon regeneration of the dialysate. Also, assuming a sorbent system similar to the REDY is utilized for dialysate regeneration having potassiumsaturated cation exchange material, the 470 millimoles of urea will displace up to 940 millimoles of potassium ion during the ion-exchange reaction in the zirconium phosphate layer. Also, assuming a session time of 3 hours, the average rate of potassium generation will be 5 millimoles per minute. Therefore, it is desired to have an electrodialysis system that can remove potassium at a rate of 5 millimoles per minute to maintain a constant dialysate potassium concentration, where the potassium ion concentration entering the dialyzer and leaving the dialyzer will therefore remain in the range of about 3.5 to about 5.0 mmol/L.

An electrodialyzer can have 10 cell pairs with 11 Neosepta CMX cation exchange membranes and 9 Neosepta AMX anion exchange membranes. Each membrane can be sized such that a total active area is from about 1900 $cm^2$ to about 4000 $cm^2$. The electrodes can be constructed of titanium with a platinum/iridium coating.

The electrodialyzer can be configured similar to FIG. 4, where the electrode rinse reservoir 58 can be filled with 250 mL to 1 L of 100 mM sodium sulfate. The concentrate reservoir 56 can be filled initially with 500 to 1.5 L of deionized water. The feed solution can be provided at a concentration of 10 mmol/L with a flow rate of 130 ml/min in some embodiments. The concentrate and electrode rinse flow loops can be recirculated at a rate of about 500 ml/min. An 8 volt DC potential is expected to be sufficient to cause adequate removal of potassium ions by electrodialysis module. Expected removal rates of potassium ion from the feed solution is from 2 to about 6 millimoles per minute potassium. It is expected that a suitable electrodialyzer module will contain about 750 mL to 2.5 L of fluid volume and total weight filled with fluid would be approximately 3 kilograms. For comparison, if fresh water was used to dilute the dialysate potassium ion concentration, more than 100 liters of water would be necessary to manage a potassium generation rate of 5 millimoles per minute for a 3 hours treatment period.

Sorbent for Potassium Removal

Dialysate exiting the potassium management system 38 as shown in FIG. 2 can pass through a potassium removing sorbent cartridge 37. The dialysate exiting the potassium management system can have a concentration around 3 millimoles per liter in certain embodiments. At a dialysate flow rate of 200 mL/minute and a session time of 180 minutes, approximately 108 millimoles of potassium will need to be removed from the dialysate in some cases. Assuming a zirconium phosphate capacity of 1 millimoles/gram for potassium, only 108 grams of zirconium phosphate may be required. If the zirconium phosphate is in the sodium form, approximately 0.6 millimoles per minute of sodium may be released from the cartridge. Therefore, if the dialysate has a sodium concentration of 140 millimole per liter, the dialysate exiting the potassium removing sorbent cartridge 37 can have a sodium concentration of approximately 143 millimoles per liter, which is within acceptable physiological levels of 120 to 160 millimoles per liter.

Hemofiltration, Hemodiafiltration and Peritoneal Dialysis Applications

Figure 9:
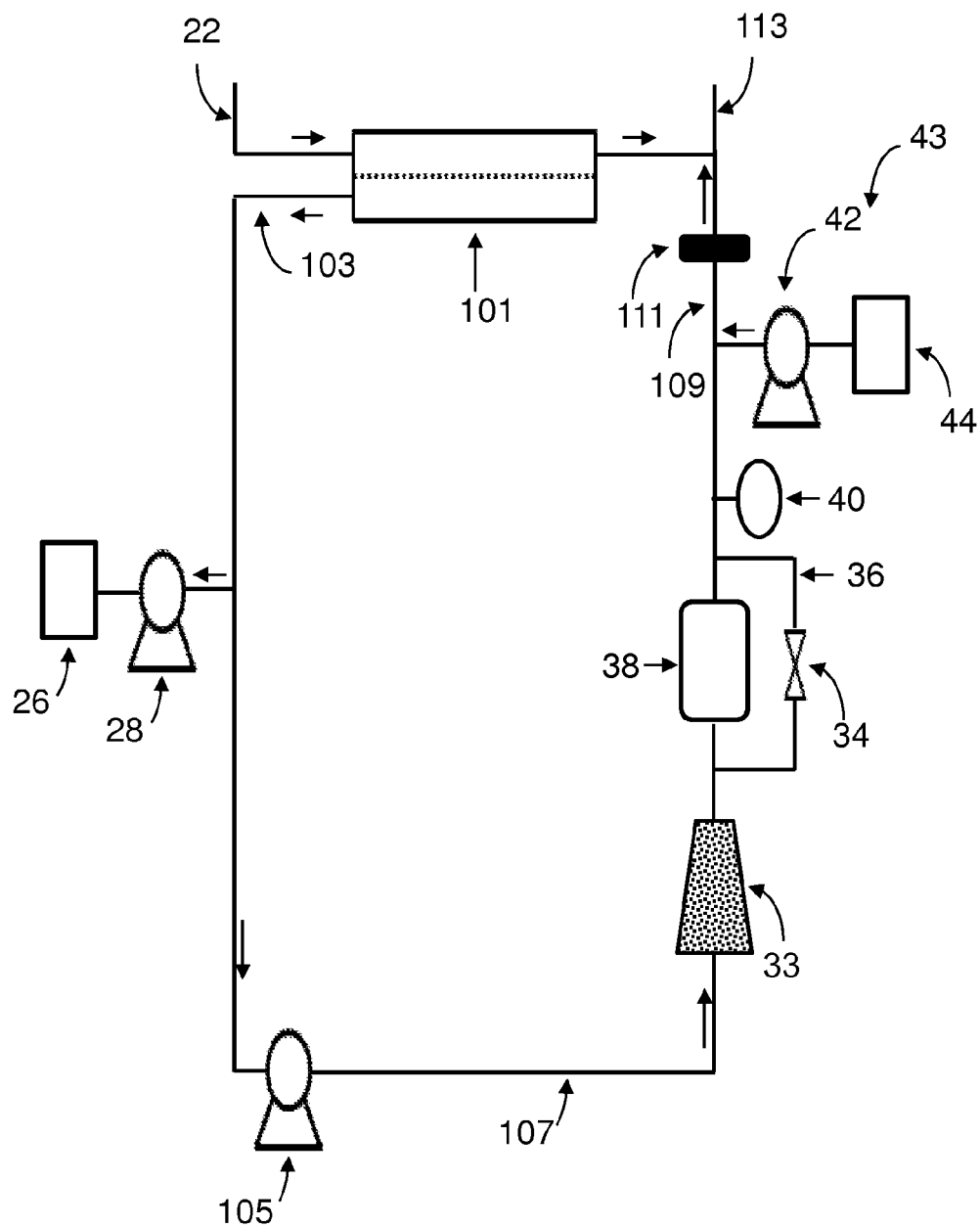
FIG. 9 is a flow diagram of a hemofiltration regeneration system with a controlled compliant filtration circuit and a potassium management system.

FIG. 9 shows a flow diagram for a hemofiltration system utilizing a filtrate regeneration unit 33 and a potassium management system 38. The blood enters via line 22 to a hemofilter 101 and a portion is filtered across membranes contained in the hemofilter 101. The hemofilter 101 can consist of a hollow-fiber dialyzer, plate-and-frame dialyzer, or other suitable hemofilters. The hemofilter 101 can contain high flux or low flux membranes made from polysulfone, polyethersulfone, poly(methyl methacrylate), cellulose, modified-cellulose or other suitable materials. The filtration pump 105 determines the amount of filtrate coming across the hemofilter. The filtrate 103 exiting the hemofilter 101 flows past an ultrafiltration pump 28 whereby ultrafiltrate is removed from the filtrate and collected in an ultrafiltration reservoir 26. The filtrate then passes through a filtrate regeneration unit 33, potassium management system 38, and infusate system 43 as described above. The regenerated filtrate 109 then passes through a microbial filter 111 before being directly infused into the blood as replacement fluid. The microbial filter 111 could include an ultrafilter filter, sterile filter, or other suitable microbial filters. The microbial filter 111 can contain membranes made from the same materials suitable for the hemofilter, preferably with pore sizes 0.2 microns or smaller. The microbial filter 111 may remove both viable organisms and endotoxin. The microbial filter 111 may be a single filter, or multiple filters, including redundant filters. The hemofiltration system shown in FIG. 9 has a controlled compliant filtrate flow loop 107. In certain embodiments, the flow loop 107 can be non-compliant or non-expandable. Hemofiltration has certain benefits over hemodialysis including higher convective clearance which increases the clearance rate of middle molecular weight species like beta-2-microglobulin.

Figure 10:
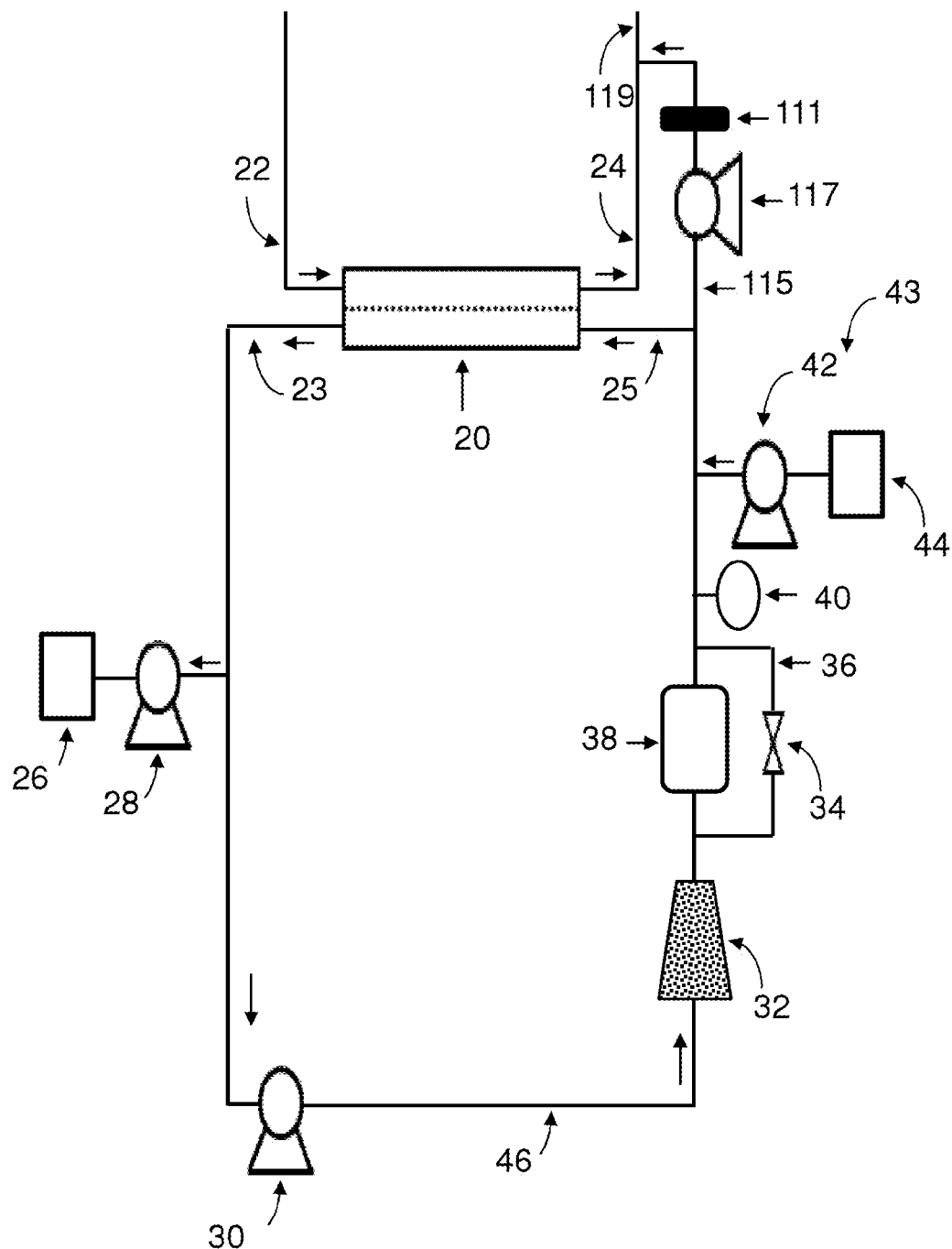
FIG. 10 is a flow diagram of a hemodiafiltration regeneration system with a controlled compliant diafiltration circuit and a potassium management system.

FIG. 10 shows a flow diagram for a hemodiafiltration system utilizing a dialysate regeneration unit 32 and a potassium management system 38. The blood enters via line 22 to a dialyzer 20 and a portion is filtered across membranes contained in the dialyzer 20. The dialyzer 20 can consist of a hollow-fiber dialyzer, plate-and-frame dialyzer, or other types of dialyzers. The dialyzer 20 can contain high flux or low flux membranes made from polysulfone, polyethersulfone, poly(methyl methacrylate), cellulose, modified-cellulose or other suitable materials. The dialysate 23 exiting the dialyzer 20 flows past an ultrafiltration pump 28 whereby a volume of fluid is removed from the dialysate and collected in an ultrafiltration reservoir 26. The dialysate is recirculated in the dialysate flow loop 46 with a dialysate pump 30. The dialysate then passes through a dialysate regeneration unit 32, potassium management system 38, and infusate system 43 as described above. A portion of the regenerated dialysate 115 is removed from the dialysate flow loop 46 with the replacement fluid pump 117 and passed through a microbial filter 111 and then directly infused into the blood as replacement fluid. The microbial filter 111 can include an ultrafilter filter, sterile filter, or other suitable microbial filters. The microbial filter 111 can contain membranes made from the same materials suitable for the dialyzer, preferably with pore sizes 0.2 microns or smaller. The microbial filter 111 may remove both viable organisms and endotoxin. The microbial filter may be a single filter, or multiple filters, including redundant filters. The hemodiafiltration system shown in FIG. 10 has a controlled compliant dialysate flow loop 46. In certain embodiments, the flow loop 46 can be non-compliant or have a non-expandable volume. Hemodiafiltration combines the benefits achieved with hemodialysis and hemofiltration, including maximum small molecule diffusive clearance and maximum middle molecule convective clearance.

Figure 11:
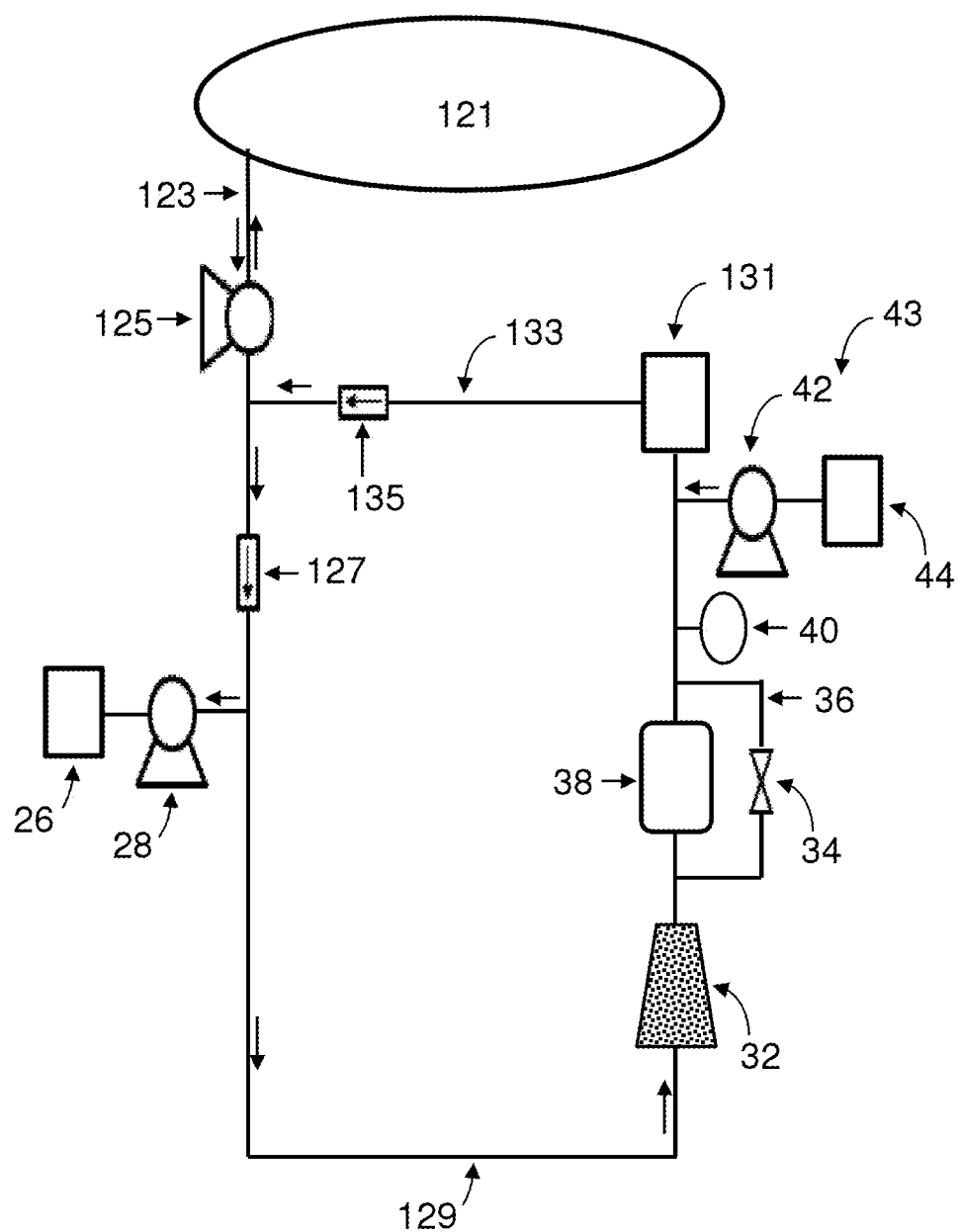
FIG. 11 is a flow diagram of a peritoneal dialysate regeneration system and a potassium management system.

FIG. 11 shows a flow diagram for a peritoneal dialysis system utilizing a dialysate regeneration unit 32 and a potassium management system 38. Initially, a patient's peritoneal cavity 121 is filled with a certain volume of dialysate. After a certain period of time, spent dialysate is drawn out of the peritoneal cavity 121 through a catheter 123 with a reversible dialysate pump 125. The spent dialysate flows through a check valve 127 and is prevented from flowing through flow line 133 because of a check valve 135. The spent dialysate continues through the dialysate regeneration unit 32 via flowpath 129 to potassium management system 38 and the infusate system 43. In the case of peritoneal dialysis, the infusate system 43 can include infusate containing high levels of glucose or icodextrin in certain embodiments. The regenerated dialysate is collected in a dialysate reservoir 131. After a desired amount of regenerated dialysate has been collected in the dialysate reservoir 131 the dialysate pump 125 is reversed and fluid is drawn out of the dialysate reservoir 131. The fluid flows through a check valve 135 and is directed through the catheter 123 back into the peritoneal cavity. Those skilled in the art will recognize that other configurations of pumps and valves can accomplish the same function, for example, valves 127 and 135 can be combined into a single 3-way valve, or pump 125 may be non-reversible if valves 127 and 135 are 2-way valves and pump 125 is placed downstream from valve 127.

This process can be continued until the dialysate regeneration system is exhausted or until the therapy is complete. At the end of a therapy, the patient will have collected a certain volume of ultrafiltrate in their peritoneal cavity. The ultrafiltrate can be removed using the ultrafiltration pump 28 and collected in the ultrafiltration reservoir 26. Likewise, during the therapy, while spent dialysate is being removed from the patient, a portion of the spent dialysate can be removed as ultrafiltrate with the ultrafiltrate pump 28. However, the amount of ultrafiltrate a patient generates is variable and depends on several factors including properties of their peritoneum, dialysate composition, and patient fluid volume, or overload. Therefore, care must be taken when operating the ultrafiltrate pump 28 during the therapy in order to avoid depleting the dialysate contained in the peritoneal cavity 121.

It will be apparent to one skilled in the art that various combinations and/or modifications and variations can be made in the dialysis system depending upon the specific needs for operation. Moreover, features illustrated or described as being part of one embodiment may be used on another embodiment to yield a still further embodiment.

What is claimed is:

1. A system for kidney replacement therapy, comprising:
a hemodialysis system having a controlled compliance dialysis circuit, a dialyzer with a dialysis membrane, a blood inlet end for receiving blood, a blood outlet end for allowing blood out of the dialyzer, a dialysate inlet end for receiving dialysate and a dialysate outlet end for allowing dialysate out of the dialyzer, wherein the blood and the dialysate contact different sides of the dialysis membrane;
a dialysate flow loop for circulating a dialysate through a dialyzer where at least one waste species enters the dialysate;
a dialysate regeneration unit containing at least one sorbent material for decreasing the concentration or conductivity of at least one waste species and releasing potassium ions to the dialysate; and
a potassium management system for modifying the potassium ion concentration of the dialysate in the dialysate flow loop, generating a potassium modified fluid, the potassium-modified fluid having a potassium ion concentration or conductivity that is higher or lower than the fluid in the dialysate flow loop; wherein at least a portion of the dialysate is conveyed through the potassium management system; and wherein the potassium management system is positioned downstream of the dialysate regeneration unit; and
a bypass line and a bypass regulator, wherein the bypass line is fluidly connected to the dialysate flow loop downstream of the dialysate regeneration unit and upstream of the potassium management system, and wherein the bypass line bypasses the potassium management system to downstream of the potassium management system;
wherein the potassium management system is an electrodialysis cell comprising at least a concentrate flow channel, a diluate flow channel and an electrode rinse flow channel, wherein potassium ions move from the diluate flow channel to the concentrate flow channel in response to an electric field, wherein the potassium-modified fluid is generated in the diluate flow channel for addition to the dialysate flow loop.

2. The system of claim 1, further comprising a deionization resin to lower the sodium ion concentration of the dialysate entering the potassium management system.

3. The system of claim 2, wherein the deionization resin substantially removes sodium ions from the dialysate entering the potassium management system.

4. The system of claim 1, wherein the potassium management system further comprises a deionization resin to lower the potassium ion concentration from the dialysate.

5. The system of claim 1, further comprising a control pump connected to an ultrafiltrate reservoir that removes or adds fluid to the dialysate flow loop downstream from the dialyzer, wherein operation of the control pump in an efflux direction causes net removal of fluid from the blood on an extracorporeal side of a membrane in the dialyzer and operation of the control pump in an influx direction causes net addition of fluid to the blood on the extracorporeal side of the membrane.

6. The system of claim 1, further comprising a potassium ion or conductivity detector that measures the conductivity or potassium ion concentration of the dialysate.

7. The system of claim 1, wherein the diluate flow channel is defined by a cation exchange membrane and an anion exchange membrane, the concentrate flow channel is defined by a cation exchange membrane and an anion exchange membrane, and an electrode rinse channel is defined by a cation exchange membrane wherein the diluate flow channel is separated from the one or more concentrate flow channel by either a cation or anion exchange membrane.

8. The system of claim 1, wherein the flow channels are defined in part by a bipolar membrane.

9. The system of claim 1, further comprising an electrode rinse pump and electrode rinse reservoir for circulating an electrode rinse solution through the electrode rinse flow channel.

10. The system of claim 1, further comprising a concentrate solution and a concentrate pump for circulating the concentrate solution through the concentrate flow channel and an electrode rinse pump and electrode rinse reservoir for circulating an electrode rinse solution through the electrode rinse flow channel.

11. The system of claim 5, wherein ultrafiltrate directed toward the ultrafiltrate reservoir passes through the potassium management system prior to collection in the ultrafiltrate reservoir.

12. The system of claim 1, wherein the dialysate flow loop further comprises a dialysate reservoir located downstream from the dialyzer and upstream from the dialysate regeneration unit.

13. The system of claim 11, wherein ultrafiltrate passes through the concentrate flow channel prior to collection in the ultrafiltrate reservoir.

14. The system of claim 1, wherein the potassium-modified fluid has a potassium ion conductivity or concentration less than the dialysate in the dialysate flow loop and thereby capable of reducing the concentration of potassium in the dialysate flow loop upon addition to the dialysate.

15. The system of claim 1, wherein the potassium management system modifies a conductivity or potassium ion concentration by application of an electrical field.

16. The system of claim 1, wherein the potassium management system generates the potassium-modified fluid from dialysate removed from the dialysate flow loop.

17. The system of claim 1, wherein potassium-modified fluid from the potassium management system is added to the dialysate flow loop at a position between an inlet of the dialyzer and an outlet of the dialysate regeneration unit.

18. The system of claim 1, wherein the potassium management system comprises a capacitive deionization cell.

19. The system of claim 18, wherein the capacitive deionization cell can store potassium ions for generating a potassium-modified fluid having a higher concentration than the fluid entering the capacitive deionization cell.

20. The system of claim 18, wherein the potassium management system comprises at least two capacitive deionization cells, wherein one capacitive deionization cell can be regenerated by passing a flushing fluid through the capacitive deionization cell while the other capacitive deionization remains operable to generate the potassium-modified fluid.

21. A method for regenerating a dialysate, comprising:
circulating a dialysate in a dialysate flow loop wherein the dialysate contacts a dialyzer and a dialysate regeneration unit containing at least one sorbent material and a waste species enters the dialysate at the dialyzer and is at least partially removed by the dialysate regeneration unit; and
modifying the potassium concentration of a provided input fluid using a potassium management system to modify the potassium concentration of the dialysate within the dialysate flow loop; wherein the potassium concentration is modified by conveying the dialysate through the potassium management system; and wherein the potassium management system is located downstream of the dialysate regeneration unit;
wherein the dialysate flow loop comprises a bypass line and a bypass regulator, wherein the bypass is fluidly connected to the dialysate flow loop downstream of the dialysate regeneration unit and upstream of the potassium management system, and wherein the bypass line bypasses the potassium management system to downstream of the potassium management system; and
wherein the potassium management system is an electrodialysis cell comprising at least a concentrate flow channel, a diluate flow channel and an electrode rinse flow channel, wherein potassium ions move from the diluate flow channel to the concentrate flow channel in response to an electric field wherein the potassium-modified fluid is generated in the diluate flow channel for addition to the dialysate flow loop.

22. The method of claim 21, wherein the potassium concentration of the provided input fluid is modified by application of an electrical field to generate the potassium-modified fluid.

23. The method of claim 22, wherein the dialysate is contacted with a deionization resin to substantially remove sodium ions from the dialysate prior to modifying the potassium concentration through application of the electric field.

24. The method of claim 21, wherein the input fluid is a fluid removed from the dialysate flow loop at a location between an outlet of the dialysate regeneration unit and an inlet of the dialyzer.

25. The method of claim 21, wherein the potassium-modified solution is added to the dialysate flow loop at a location between an outlet of the dialysate regeneration unit and an inlet of the dialyzer.

26. The method of claim 21, further comprising operating a control or ultrafiltration pump to remove or add fluid-to or ultrafiltrate-from the dialysate flow loop downstream from the dialyzer, wherein operation of the control pump in an efflux direction causes net removal of fluid from the blood on an extracorporeal side of a membrane in the dialyzer and operation of the control pump in an influx direction causes net addition of fluid to the blood on the extracorporeal side of the membrane.

27. The method of claim 26, further comprising operating the control pump to transport ultrafiltrate through the concentrate flow channel of the potassium management system to a waste reservoir.

28. The method of claim 21, wherein the dialysate regeneration contains a sorbent having potassium ions for cation exchange with the waste species.

29. The method of claim 21, further comprising a potassium management system that modifies the potassium concentration of the dialysate by adding the potassium-modified fluid to the dialysate flow loop.

30. The system of claim 1, wherein the system is controlled compliant.

31. The system of claim 1, wherein the system selectively meters fluid into and out of the dialysate flow loop.

32. The system of claim 1, wherein the system selectively meters fluid into and out of the dialysate flow loop using any one of a control pump, a water pump, a salination pump, an acid concentrate pump, a replacement fluid pump, and combinations thereof.

33. The system of claim 1, wherein the system provides for bi-directional flow.

34. The method of claim 21, wherein the method is controlled compliant.

35. The method of claim 21, wherein fluid is selectively metered into and out of the dialysate flow loop.

36. The method of claim 21, wherein the fluid is selectively metered into and out of the dialysate flow loop using any one of a control pump, a water pump, a salination pump, an acid concentrate pump, a replacement fluid pump, and combinations thereof.

37. he method of claim 21, wherein bi-directional flow is provided with the dialysate flow loop.

* * * * *